(12) United States Patent
Lanier

(10) Patent No.: US 9,956,239 B2
(45) Date of Patent: *May 1, 2018

(54) METHODS OF TREATING RETROVIRAL INFECTIONS AND RELATED DOSAGE REGIMES

(71) Applicant: Chimerix, Inc., Durham, NC (US)

(72) Inventor: Ernest Randall Lanier, Chapel Hill, NC (US)

(73) Assignee: Chimerix, Inc., Durham, NC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/628,064

(22) Filed: Jun. 20, 2017

(65) Prior Publication Data

US 2017/0281658 A1 Oct. 5, 2017

Related U.S. Application Data

(63) Continuation of application No. 15/044,810, filed on Feb. 16, 2016, now Pat. No. 9,694,024, which is a continuation of application No. 13/642,985, filed as application No. PCT/US2011/033979 on Apr. 26, 2011, now Pat. No. 9,278,135.

(60) Provisional application No. 61/413,079, filed on Nov. 12, 2010, provisional application No. 61/405,084, filed on Oct. 20, 2010, provisional application No. 61/381,356, filed on Sep. 9, 2010, provisional application No. 61/333,607, filed on May 11, 2010, provisional application No. 61/328,491, filed on Apr. 27, 2010, provisional application No. 61/327,919, filed on Apr. 26, 2010, provisional application No. 61/327,914, filed on Apr. 26, 2010.

(51) Int. Cl.

| A61K 31/675 | (2006.01) |
|---|---|
| A61K 31/685 | (2006.01) |
| A61K 31/52 | (2006.01) |
| A61K 31/662 | (2006.01) |
| A61K 45/06 | (2006.01) |
| A61K 47/54 | (2017.01) |
| A61K 47/48 | (2006.01) |

(52) U.S. Cl.
CPC ........... A61K 31/685 (2013.01); A61K 31/52 (2013.01); A61K 31/662 (2013.01); A61K 45/06 (2013.01); A61K 47/48023 (2013.01); A61K 47/48053 (2013.01); A61K 47/54 (2017.08)

(58) Field of Classification Search
USPC ......................................................... 514/81
See application file for complete search history.

(56) References Cited

U.S. PATENT DOCUMENTS

| 1,944,530 A | 1/1934 | Schonburg |
| 3,422,021 A | 1/1969 | Roy |
| 3,468,935 A | 9/1969 | Peck |
| 4,327,039 A | 4/1982 | Blum et al. |
| 4,444,766 A | 4/1984 | Bosies et al. |
| 4,562,179 A | 12/1985 | Teraji et al. |
| 4,619,794 A | 10/1986 | Hauser |
| 4,705,651 A | 11/1987 | Staibano |
| 4,870,063 A | 9/1989 | Binderup et al. |
| 4,927,814 A | 5/1990 | Gall et al. |
| 5,043,437 A | 8/1991 | Khorlin et al. |
| 5,047,533 A | 9/1991 | Reist et al. |
| 5,142,051 A | 8/1992 | Holy et al. |
| 5,183,815 A | 2/1993 | Saari et al. |
| 5,194,654 A | 3/1993 | Hostetler et al. |
| 5,196,409 A | 3/1993 | Breuer et al. |
| 5,223,263 A | 6/1993 | Hostetler et al. |
| 5,247,085 A | 9/1993 | Harnden et al. |
| 5,300,671 A | 4/1994 | Tognella et al. |
| 5,300,687 A | 4/1994 | Schwender et al. |
| 5,312,954 A | 5/1994 | Breuer et al. |

(Continued)

FOREIGN PATENT DOCUMENTS

| CN | 1810816 A | 8/2006 |
| CS | 220713 B1 | 4/1983 |

(Continued)

OTHER PUBLICATIONS

Aldern et al. "Increased Antiviral Activity of 1-O-Hexadecyloxypropyl-[2-14C]Cidofovir in MRC-5 Human Lung Fibroblasts is Explained by Unique Cellular Uptake and Metabolism" *Mol. Pharmacol.* 63.3(2003):678-681.

Andrei et al. "Activities of Various Compounds against Murine and Primate Polyomaviruses" *Antimicrob. Agents Chemother.* 41.3(1997):587-593.

Annaert et al. "*In Vitro, Ex Vivo*, and *In Situ* Intestinal Absorption Characteristics of the Antiviral Ester Prodrug Adefovir Dipivoxil" *J. Pharm. Sci.* 89.8(2000):1054-1062.

(Continued)

*Primary Examiner* — Rei Tsang Shiao
(74) *Attorney, Agent, or Firm* — COOLEY LLP; Ivor R. Elrifi; Heidi A. Erlacher

(57) ABSTRACT

The present invention relates to compounds and methods for treating retroviral infections and/or Hepatitis B viral infections. Some compounds of the invention are described by Formula I:

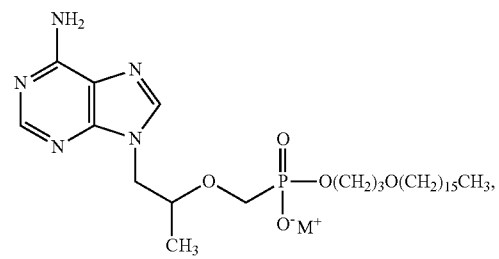

or a stereoisomer, a diastereomer, an enantiomer or racemate thereof.

20 Claims, 13 Drawing Sheets

(56) References Cited

U.S. PATENT DOCUMENTS

| | | | |
|---|---|---|---|
| 5,395,826 A | 3/1995 | Naumann et al. |
| 5,411,947 A | 5/1995 | Hostetler et al. |
| 5,428,181 A | 6/1995 | Sugioka et al. |
| 5,442,101 A | 8/1995 | Hanhijarvi et al. |
| 5,463,092 A | 10/1995 | Hostetler et al. |
| 5,476,938 A | 12/1995 | Vemishetti et al. |
| 5,484,809 A | 1/1996 | Hostetler et al. |
| 5,484,911 A | 1/1996 | Hong et al. |
| 5,512,671 A | 4/1996 | Piantadosi et al. |
| 5,532,226 A | 7/1996 | Demarest et al. |
| 5,591,852 A | 1/1997 | Vemishetti et al. |
| 5,614,548 A | 3/1997 | Piantadosi et al. |
| 5,627,185 A | 5/1997 | Gosselin et al. |
| 5,650,510 A | 7/1997 | Webb, II et al. |
| 5,656,745 A | 8/1997 | Bischofberger et al. |
| 5,663,159 A | 9/1997 | Starrett, Jr. et al. |
| 5,672,697 A | 9/1997 | Buhr et al. |
| 5,696,277 A | 12/1997 | Hostetler et al. |
| 5,717,095 A | 2/1998 | Arimilli et al. |
| 5,744,461 A | 4/1998 | Hostetler et al. |
| 5,744,592 A | 4/1998 | Hostetler et al. |
| 5,756,711 A | 5/1998 | Zilch et al. |
| 5,760,013 A | 6/1998 | Hwu et al. |
| 5,770,584 A | 6/1998 | Kucera et al. |
| 5,780,617 A | 7/1998 | van den Bosch et al. |
| 5,792,756 A | 8/1998 | Starrett, Jr. et al. |
| 5,798,340 A | 8/1998 | Bischofberger et al. |
| 5,817,638 A | 10/1998 | Hostetler |
| 5,827,831 A | 10/1998 | Hostetler et al. |
| 5,840,716 A | 11/1998 | Ubasawa et al. |
| 5,854,228 A | 12/1998 | Webb, II et al. |
| 5,856,314 A | 1/1999 | Kaas et al. |
| 5,869,468 A | 2/1999 | Freeman |
| 5,877,166 A | 3/1999 | Reist et al. |
| 5,885,973 A | 3/1999 | Papapoulos et al. |
| 5,886,179 A | 3/1999 | Arimilli et al. |
| 5,922,695 A | 7/1999 | Arimilli et al. |
| 5,922,696 A | 7/1999 | Casara et al. |
| 5,935,946 A | 8/1999 | Munger, Jr. et al. |
| 5,962,437 A | 10/1999 | Kucera et al. |
| 5,977,061 A | 11/1999 | Holy et al. |
| 5,977,089 A | 11/1999 | Arimilli et al. |
| 6,002,029 A | 12/1999 | Hostetler et al. |
| 6,030,960 A | 2/2000 | Morris-Natschke et al. |
| 6,043,230 A | 3/2000 | Arimilli et al. |
| 6,069,249 A | 5/2000 | Arimilli et al. |
| 6,194,388 B1 | 2/2001 | Krieg et al. |
| 6,207,646 B1 | 3/2001 | Krieg et al. |
| 6,218,371 B1 | 4/2001 | Krieg et al. |
| 6,225,292 B1 | 5/2001 | Raz et al. |
| 6,239,116 B1 | 5/2001 | Krieg et al. |
| 6,252,060 B1 | 6/2001 | Hostetler |
| 6,448,392 B1 | 9/2002 | Hostetler et al. |
| 6,562,798 B1 | 5/2003 | Schwartz |
| 6,589,940 B1 | 7/2003 | Raz et al. |
| 6,605,602 B1 | 8/2003 | Vats |
| 6,635,472 B1 | 10/2003 | Lauermann |
| RE38,333 E | 11/2003 | Arimilli et al. |
| 6,670,341 B1 | 12/2003 | Kucera et al. |
| 6,716,825 B2 | 4/2004 | Hostetler et al. |
| 6,818,629 B2 | 11/2004 | Peterson et al. |
| 7,026,469 B2 | 4/2006 | Kucera et al. |
| 7,034,014 B2 | 4/2006 | Hostetler et al. |
| 7,094,772 B2 | 8/2006 | Hostetler et al. |
| 7,098,197 B2 | 8/2006 | Hostetler et al. |
| 7,288,265 B1 | 10/2007 | Rolf |
| 7,390,791 B2 | 6/2008 | Becker et al. |
| 7,452,898 B2 | 11/2008 | Hostetler et al. |
| 7,553,932 B1 | 6/2009 | Von Herrath et al. |
| 7,652,001 B2 | 1/2010 | Hostetler et al. |
| 7,749,983 B2 | 7/2010 | Hostetler et al. |
| 7,790,703 B2 | 9/2010 | Hostetler et al. |
| 7,799,782 B2 | 9/2010 | Munson et al. |
| 8,993,542 B2 | 3/2015 | Lanier et al. |
| 9,278,135 B2 * | 3/2016 | Lanier ............... A61K 31/52 |
| 9,694,024 B2 * | 7/2017 | Lanier ............... A61K 31/52 |
| 2003/0211072 A1 | 11/2003 | Carreno-Gomez et al. |
| 2004/0019232 A1 | 1/2004 | Hostetler et al. |
| 2004/0022873 A1 | 2/2004 | Guilford et al. |
| 2004/0071757 A1 | 4/2004 | Rolf |
| 2004/0161398 A1 | 8/2004 | Kucera et al. |
| 2004/0224917 A1 | 11/2004 | Dahl et al. |
| 2004/0259845 A1 | 12/2004 | Kucera et al. |
| 2005/0187192 A1 | 8/2005 | Fleming et al. |
| 2005/0261237 A1 | 11/2005 | Boojamra et al. |
| 2006/0128692 A1 | 6/2006 | Chen et al. |
| 2006/0263355 A1 | 11/2006 | Quan et al. |
| 2007/0003516 A1 | 1/2007 | Almond et al. |
| 2007/0003608 A1 | 1/2007 | Almond et al. |
| 2007/0026056 A1 | 2/2007 | Rolf |
| 2007/0105812 A1 | 5/2007 | Kucera et al. |
| 2008/0009462 A1 | 1/2008 | Hostetler et al. |
| 2008/0020018 A1 | 1/2008 | Moodley et al. |
| 2008/0161324 A1 | 7/2008 | Johansen et al. |
| 2009/0017448 A1 | 1/2009 | Toth et al. |
| 2009/0087451 A1 | 4/2009 | Buller |
| 2009/0111774 A1 | 4/2009 | Tokars et al. |
| 2010/0173870 A1 | 7/2010 | Hostetler et al. |
| 2010/0249056 A1 | 9/2010 | Hostetler et al. |
| 2011/0021464 A1 | 1/2011 | Lanier et al. |
| 2013/0035313 A1 | 2/2013 | Almond et al. |
| 2014/0011769 A1 | 1/2014 | Lanier |

FOREIGN PATENT DOCUMENTS

| | | |
|---|---|---|
| EP | 0186405 A2 | 7/1986 |
| EP | 0253412 A2 | 1/1988 |
| EP | 0632048 A1 | 1/1995 |
| EP | 0753523 A1 | 1/1997 |
| EP | 0897709 A1 | 2/1999 |
| EP | 1438962 A1 | 7/2004 |
| EP | 1914237 A2 | 4/2008 |
| GB | 1280788 A | 7/1972 |
| JP | 61152694 A | 7/1986 |
| JP | 10029998 A | 2/1998 |
| WO | WO-9105558 A1 | 5/1991 |
| WO | WO-9109602 A2 | 7/1991 |
| WO | WO-9520980 A1 | 8/1995 |
| WO | WO-96033200 A1 | 10/1996 |
| WO | WO-9640088 A1 | 12/1996 |
| WO | WO-9818810 A1 | 5/1998 |
| WO | WO-9838202 A1 | 9/1998 |
| WO | WO-9908685 A1 | 2/1999 |
| WO | WO-0004032 A1 | 1/2000 |
| WO | WO-0006588 B1 | 4/2000 |
| WO | WO-0037477 A1 | 6/2000 |
| WO | WO-0112223 A3 | 9/2001 |
| WO | WO-0021556 A9 | 10/2001 |
| WO | WO-0122990 A3 | 10/2001 |
| WO | WO-0139724 A3 | 10/2001 |
| WO | WO-03030934 A2 | 4/2003 |
| WO | WO-03049746 A2 | 6/2003 |
| WO | WO-04062600 A2 | 7/2004 |
| WO | WO-04112718 A3 | 4/2005 |
| WO | WO-05087788 A2 | 9/2005 |
| WO | WO-05121378 A2 | 12/2005 |
| WO | WO-06017044 A2 | 2/2006 |
| WO | WO-06066074 A2 | 6/2006 |
| WO | WO-06076015 A2 | 7/2006 |
| WO | WO-06110655 A2 | 10/2006 |
| WO | WO-06110656 A2 | 10/2006 |
| WO | WO-0122972 A9 | 12/2006 |
| WO | WO-06130217 A2 | 12/2006 |
| WO | WO-2007034173 A1 | 3/2007 |
| WO | WO-07130783 A2 | 11/2007 |
| WO | WO-08007392 A2 | 1/2008 |
| WO | WO-08033466 A2 | 3/2008 |
| WO | WO-08118013 A2 | 10/2008 |
| WO | WO-08133966 A1 | 11/2008 |
| WO | WO-08133982 A2 | 11/2008 |
| WO | WO-08144743 A1 | 11/2008 |
| WO | WO-09082818 A1 | 7/2009 |
| WO | WO-09082819 A1 | 7/2009 |
| WO | WO-09094190 A2 | 7/2009 |

(56) References Cited

FOREIGN PATENT DOCUMENTS

| WO | WO-09094191    | 7/2009 |
|----|----------------|--------|
| WO | WO-11011519 A1 | 1/2011 |
| WO | WO-11017253 A1 | 2/2011 |
| WO | WO-11053812 A1 | 5/2011 |
| WO | WO-11115914 A1 | 9/2011 |
| WO | WO 2014/035945 A1 | 3/2014 |

OTHER PUBLICATIONS

Balzarini et al. "Antiretrovirus Activity of a Novel Class of Acyclic Pyrimidine Nucleoside Phosphonates" *Antimicrob. Agents Chemother.* 45.7(2002):2185-2193.

Bartlett et al. "Phase I Trial of Doxorubicin with Cyclosporine as a Modulator of Multidrug Resistance" *J. Clin. Oncol.* 12.4(1994):835-842.

Beadle et al. "Alkoxyalkyl Esters of Cidofovir and Cyclic Cidofovir Exhibit Mutiple-Log Enhancement of Antiviral Activity Against Cytomegalovirus and Herpes Virus Replication In Vitro" *Antimicrob Agents Chemother.* 46.8(2002):2381-2386.

Berge et al. "Pharmaceutical Salts" *J. Pharmaceutical Sci.* 66.1(1977):1-19.

Bidanset et al. "Oral Activity of Ether Lipid Ester Prodrugs of Cidofovir against Experimental Human Cytomegalovirus Infection" *J. Infect. Dis.* 190.3(2004):499-503.

Biron. "Antiviral Drugs for Cytomegalovirus Diseases" *Antiviral Res.* 71(2006):154-163.

Blasco et al. "Extracellular Vaccinia Virus Formation and Cell-to-Cell Virus Transmission are Prevented by Deletion of the Gene Encoding the 37,000-Dalton Outer Envelope Protein" *J. Virol.* 65.11(1991):5910-5920.

Borroto-Esoda et al. "*In vitro* Evaluation of the Anti-HIV Activity and Metabolic Interactions of Tenofovir and Emtricitabine" *Antiviral Ther.* 11. 3(2006):377-384.

Boyer et al. "The Nucleoside Analogs 4'C-Methyl Thymidine and 4'C-Ethyl Thymidine Block DNA Synthesis by Wild-type HIV-1 RT and Excision Proficient NRTI Resistant RT Variants" *J. of Mol. Biol.*, 2007, 371:873-882.

Bray et al. "Antiviral Prophylaxis of Smallpox" *J. Antimicrob. Chemother.* 54.1(2004):1-5.

Buller et al. "Efficacy of Oral Active Ether Lipid Analogs of Cidofovir in a Lethal Mousepox Model" *Virol.* 318.2(2004):474-481.

Buller et al. "Efficacy of Smallpox Vaccination in the Presence of Antiviral Drugs, Cidofovir, and Hexadecyoxypropylcidofovir" Antiviral Res. 65.3(2005):A80. (Abstract #72).

Ciesla et al. "Esterification of Cidofovir with Alkoxyalkanols Increases Oral Bioavailability and Diminishes Drug Accumulation in Kidney" *Antiviral Res.* 59.3(2003):163-171.

Cihlar et al. "Design and Profiling of GS-9148, a Novel Nucloetide Analog Active Against Nucleoside-Resistant Variants of Human Immunodeficiency Virus Type 1, and Its Orally Bioavailable Phosphonoamidate Prodrug, GS-9131" *Antimicrob. Agents Chemother.*52.2(2008):655-665.

Collier, A.C., "Efficacy of Combination Antiretroviral Therapy", *Antiviral Chemotherapy*, 4:355-372 (1996).

Connelly et al. "Mechanism of Uptake of the Phosphonate Analog (S)-1-(3-hydroxy-2-phosphonylmethoxy-propyl)Cytosine (HPMPC) in Vero Cells" *Biochem. Pharma.* 46.6(1993):1053-1057.

"Creating Orally Available Medicines from Bioactive Molecules" *Presentation at BIG 2004 Annual International Convention* (Jun. 7, 2004).

Dal Pozzo et al. "In Vitro Evaluation of the Anti-orf Virus Activity of Alkoxyalkyl Esters of CDV, cDV and (S)-HPMPA" *Antiviral Res.* 75(2007):52-57.

De Clercq et al. "Therapeutic Potential of Nucleoside/Nucleotide Analogues Against Poxvirus Infections" *Rev. Med. Virol.* 14.5(2004):289-300.

De Clercq "Antiviral Drugs in Current Clinical Us." *J. Virol.* 30.2(2004):115-133.

De Clercq "Clinical Potential of the Acyclic Nucleoside Phosphonates Cidofovir, Adefovir, and Tenofovir in Treatment of DNA Virus and Retrovirus Infections." *Clin. Microbiol. Rev.* 16.4(2003):569-596.

De Clercq "The Acyclic Nucleoside Phosphonates from Inception to Clinical Use: Historical Perspective" *Antiviral Res.* 75(2007):1-13.

De Clercq "Vaccinia Virus Inhibitors as a Paradigm for the Chemotherapy of Poxvirus Infections" *Clin. Microbiol. Rev.* 14.2(2001):382-397.

Delaney et al. "Combinations of Adefovir with Nucleoside Analogs Produce Additive Antiviral Effects against Hepatitis B Virus in Vitro" *Antimicrob. Agents Chemother.* 48.10(2004):3702-3710.

Denes et al. "Main Adult Herpes Virus Infections of the CNS" *Anti-Infective Therapy* 3.4(2005):663-678.

Fardis et al. "Case Study: Tenofovir Disoproxil Fumarate: An Oral Prodrug of Tenofovir" *Volume V: Prodrugs: Challenges and Rewards Part 1. Biotechnology, Pharmaceutical Aspects.* 5.20(2007):649-657.

Fisher et al. "Phase I Trial of Etoposide with the Cyclosporine SDZ PSC 833, a Modulator of Multidrug Resistance (MDR)" *Proc. Am Soc. Clin. Oncol.* 12(1994):143. (Abstract #368).

Franchetti et al. "Inhibition of HIV-1 Replication in Machrophages by Red Blood Cell-Mediated Delivery of a Heterodinucleotide of Lamivudine and Tenofovir" *Nucleosides Nucleotides Nucleic Acids.* 26.8-9(2007):953-957.

Fung et al. "Tenofovir Disoproxil Fumarate: A Nucleotide Reverse Transcriptase Inhibitor for the Treatment of HIV Infection" *Clin. Ther.* 24.10(2002):1515-1548.

Gallant et al. "Tenofovir disoproxil fumarate (Viread®) for the Treatment of HIV Infection" *Expert Rev. Anti-infect. Ther.* 1.3(2003):415-422.

Gauvry et al. "Dealkylation of Dialkyl Phosphonates with Boron Tribromide" *Synthesis* 4(2001):553-554.

Hammond et al. "Alkylglycerol Prodrugs of Phosphonoformate are Potent In Vitro Inhibitors of Nucleoside-Resistant Human Immunodeficiency Virus Type 1 and Select for Resistance Mutations that Suppress Zidovudine Resistance" *Antimicrob. Agents Chemother.* 45.6(2001):1621-1628.

Hartline et al. "Ether Lipid-Ester Prodrugs of Acyclic Nucleoside Phosphonates: Activity Against Adenovirus Replication In Vitro" *J. Infect. Dis.* 191.3(2005):396-399.

Held et al. "Treatment of BK Virus-Associated Hemorrhagic Cystitis and Simultaneous CMV Reactivation with Cidofovir" *Bone Marrow Transplant.* 26(2000):347-350.

Hillenkamp et al. "Topical Treatment of Acute Adenoviral Keratoconjunctivitis With 0.2% Cidofovir and 1% Cyclosporine" *Arch. Ophthalmol.* 119.10(2001):1487-1491.

Hockova et al. "5-Substituted-2,4-diamino-642-(phosphonomethoxy)ethoxy]pyrimidines—Acyclic Nucleoside Phosphonate Analogues with Antiviral Activity" *J. Med. Chem.* 46.23(2003):5064-5073.

Holy et al. "6-[2-(Phosphonomethoxy)alkoxy]pyrimidines With Antiviral Activity" *J. Med. Chem.* 45.9(2002):1918-1929.

Holy et al. "Structure-Antiviral Activity Relationship in the Series of Pyrimidine and Purine N-[2(2-Phosphonomethoxy)ethyl] Nucleotide Analogues" J. *Med. Chem.* 42.12(1999):2064-2086.

Holy "Phosphonomethoxyalkyl Analogs of Nucleotides" *Curr. Pharma Des.* 9.31(2003):2567-2592.

Holy "Simple Method for Cleavage of Phosphonic Acid Diesters to Monoesters" *Synthesis* 4(1998):381-385.

Hostetler et al. "Enhanced Antiproliferative Effects of Alkoxyalkyl Esters of Cidofovir in Human Cervical Cancers Cells *in vitro*" *Mol. Cancer Ther.* 5.1(2006):156-159.

Hostetler "Alkoxyalkyl Prodrugs of Acyclic Nucleoside Phosphonates Enhance Oral Antiviral Activity and Reduce Toxicity: Current State of the Art" *Antiviral Res.* 82.2(2009):A84-A98.

Hostetler, K.Y. et al., "Alkoxyalkyl Esters of (S)-9-[3-Hydroxy-2-(Phosphonomethoxy)Propyl]Adenine Are Potent Inhibitors of the Replication of Wild-Type and Drug-Resistant Human Immunodeficiency Virus Type 1 In Vitro", *Antimicrobial Agents and Chemotherapy*, 50(8):2857-2859 (2006).

Hostetler, K., "In vitro and in vivo evaluation of hexadecyloxypropyl-9-R-[2-(phosphono-methoxy) propyl]adenine

(56) References Cited

OTHER PUBLICATIONS as a potential treatment of HIV-1 infection", *Global Antiviral Journal*, Abstract 84, 2(2):96-97 (2006).

Huggins et al. "Cidofovir Treatment of Variola (Smallpox) in the Hemorrhagic Smallpox Primate Model and the IV Monkeypox Primate Model" *Antiviral Res.* 57.3(2003):A78. (Abstract #127).

Huggins et al. "Orally Active Ether Lipid Prodrugs of Cidofovir for the Treatment of Smallpox" *Antiviral Res.* 53(2002):A66. (Abstract #104).

Huggins et al. "Successful Cidofovir Treatment of Smallpox-Like Disease in Variola and Monkeypox Primate Models" *Antiviral Res.* 62.2(2004):A57-A58. (Abstract #76).

Hurwitz Selwyn J. et al. "Practical Considerations for Developing Nucleoside Reverse Transcriptase Inhibitors" *Drug Discovery Today: Technologies*, 2012; 9(3):e183-e193. doi:10.1016/j.ddtec.2012.09.003. Available online Oct. 5, 2012.

Jacobson "Treatment of Cytomegalovirus Retinitis in Patients with the Acquired Immunodeficiency Syndrome" *Drug Ther.* 337(1997):105-114.

Jasko et al. "A New Approach to Synthesis of 5'-O-phosphonomethyl Derivatives of Nucleosides and Their Analogues" *Bioorganicheskaya Khimiya.* 20.1(1994):50-54. (English Abstract Only).

Josephson et al. "Polyomavirus-Associated Nephropathy: Update on Antiviral Strategies" *Transpl. Infect. Dis.* 8(2006):95-101.

Kearney et al. "Tenofovir Disoproxil Fumarate: Clinical Pharmacology and Pharmacokinetcs" *Clin. Pharmacokinet.* 43.9(2004):595-612.

Keith et al. "Evaluation of Nucleoside Phosphonates and Their Analogs and Prodrugs for Inhibition of Orthopoxvirus Replication" *Antimicrob Agents Chemother.* 47.7(2003):2193-2198.

Keith et al. "Inhibitory Activity of Alkoxyalkyl and Alkyl Esters of Cidofovir and Cyclic Cidofovir Against Orthopoxvirus Replication In Vitro" *Antimicrob. Agents Chemother.* 48.5(2004):1869-1871.

Kern et al. "Enhanced Inhibition of Orthopoxvirus Replication In Vitro by Alkoxyalkyl Esters of Cidofovir and Cyclic Cidofovir" *Antimicrob. Agents Chemother.* 46.4(2002):991-995.

Kern et al. "Oral Treatment of Murine Cytomegalovirus Infections with Ether Lipid Esters of Cidofovir" *Antimicrob Agents Chemother.* 48.9(2004):3516-3522.

Kini et al. "Alkoxy Propane Prodrugs of Foscarnet: Effect of Alkyl Chain Length on In Vitro Antiviral Activity in Cells Infected with HIV-1, HSV-1 and HCMV" *Antiviral Res.* 36.1(1997):43-53.

Kornbluth et al. "Mutations in the E9L Polymerase Gene of Cidofovir-Resistant Vaccinia Virus Strain WR are Associated with the Drug Resistance Phenotype" *Antimicrob. Agents Chemother.* 50.12(2006):4038-4043.

Lanier Randall et al. "Oral Session 3: Retroviruses; 89, Development of Hexadecyloxypropyl Tenofovir (CMX157) for HIV: Potential for Use as a Microbicide and Therapeutic" *Antiviral Research*, 2009; 82 (2), A43. doi:10.1016/jantiviral.2009.02.094. Available online May 4, 2009. Retrieved from the Internet: URL:http://ac.els-cdn.com/S0166354209001211 /1-s2.0-S0166354209001211-main.pdf?tid=6a01 dd98-cb43-11e5-8078-00000aacb360&acdnat=1454592790049bf6886287acb01ce493dd31d4ebaa.

Lanier et al. "Development of Hexadecyloxypropyl Tenofovir (CMX157) for Treatment of Infection Caused by Wild-Type and Nucleoside/Nucleoside-Resistant HIV." *Antimicrob. Agents Chemother.* 54.7(2010):2901-2909.

Lebeau et al. "Activities of Alkoxyalkyl Esters of Cidofovir (CDV), Cyclic CDV, and (S)-9(3- Hydroxy-2-Phosphonylmethoxypropyl) Adenine Against Orthopoxviruses in Cell Monolayers and in Organotypic Cultures." *Antimicrob. Agents Chemother.* 50.7(2006):2525-2529.

Levin Jules "CMX157 Conjugate of tenofovir, prodrug: Hexadecyloxypropyl Tenofovir Associates Directly with HIV and Subsequently Inhibits Viral Replication in Untreated Cells" *Conference on Retroviruses and Opportunistic Infections Montreal, Canada*, Feb. 8-11, 2009; 7 pages. Retrieved from the Internet: URL:http://www.natap.org/2009/CROI/croi_84.htm.

Lu et al. "Intraocular Properties of Hexadecyloxypropyl-Cyclic-Cidofovir in Guinea Pigs" *J. Ocul. Pharmacol. Ther.* 21.3(2005):205-209.

Lyseng-Williamson et al. "Tenofovir Disproxil Fumarate: A Review of its Use in the Management of HIV Infection." *Drugs.* 65.3(2005):413-432.

Madeddu et al. "Renal Toxicity in HIV-Infected Patients Receiving HAART Including Tenofovir" *Infez. Med.* 14.3(2006):125-134. (Italian Original and English Abstract).

Michaud et al. "The Dual Role of Pharmacogenetics in HIV Treatment: Mutations and Polymorphisms Regulating Antiretroviral Drug Resistance and Disposition" *Pharm. Rev* 64.3(2012):803-833.

Myrick et al. "The Triple Combination of Tenofovir, Emtricitabine and Efavirenz Shows Synergistic Anti-HIV-1 Activity In Vitro" *Antiviral Res.* 74. 3(2007): A61. (Abstract #83).

Niemi et al. "Bisphosphonate Prodrugs: Synthesis and in Vitro Evaluation of Novel Acyloxyalkyl Esters of Clodronic Acid" *J Med. Chem.* 42.24(1999):5053-5058.

Painter et al. "Biochemical and Mechanistic Basis for the Activity of Nucleoside Analogue Inhibitors of HIV Reverse Transcriptase" *Curr. Topics Med. Chem.* 4.10(2004):1035-1044.

Painter et al. "Design and Development of Oral Drugs for the Prophylaxis and Treatment of Smallpox Infection" *Trends Biotechnot* 22.8(2004):423-427.

Painter et al. "Evaluation of Hexadecyloxypropyl-9-R-[2-(Phosphonomethoxy)propyl]-adenine, CMX157, as a Potential Treatment for Human Immunodeficiency Virus Type 1 and Hepatitis B Virus Infections" *Antimicrob. Agents Chemother.* 51.10(2007):3505-3509.

Parker et al. "Efficacy of Therapeutic Intervention with an Oral Ether-Lipid Analogue of Cidofovir (CMX001) in a Lethal Mousepox Model" *Antiviral Res.* 77.1(2008):39-49.

Portilla et al. "Progressive Multifocal Leukoencephalopathy Treated with Cidofovir in HIV-Infected Patients Receiving Highly Active Anti-Retroviral Therapy" *J. Infect.* 41(2000):182-184.

Postma et al. "Cost-Effectiveness of Antenatal HIV-Testing: Reviewing its Pharmaceutical and Methodological Aspects" *Expert Opin. Pharmacother.* 5.3(2004):521-528.

Quenelle et al. "Oral Treatment of Cowpox and Vaccinia Virus Infections in Mice with Ether Lipid Esters of Cidofovir" *Antimicrob. Agents Chemother.* 48.2(2004):404-412.

Quenelle et al. "Oral Treatment of Cowpox and Vaccinia Virus Infections in Mice with Ether Lipid Esters of Cidofovir" *Antimicrob. Agents Chemother.* 48.2(2004):404-412. Erratum in: *Antimicrob. Agents Chemother.* 48.5(2004): 1919.

Quenelle et al. "Synergistic Efficacy of the Combination of ST-246 With CMX001 Against Orthopoxviruses" *Antimicrob. Agents Chemother.* 51.11(2007):4118-4124.

Randhawa et al. "Ether Lipids Ester Derivatives of Cidofovir Inhibit Polyomavirus BK Replication In Vitro" *Antimicrob. Agents Chemother.* 50.4(2006):1564-1566.

Ray "Lack of Metabolic and Antiviral Drug Interaction Between Tenofovir, Abacavir and Lamivudine" *Antiviral Ther.* 10.3(2005):451-457.

Remichkova et al. "Synergistic Combination Effect of Cidofovir and Idoxuridine on Vaccinia Virus Replication" *Antiviral Res.* 65.3(2005):A80-A81. (Abstract #74).

Rogers "A General Synthesis of Phosphonic Acid Dichlorides Using Oxalyl Chloride and DMF Catalysis" *Tetrahed. Lett.* 33.49(1992):7473-7474.

Saady et al. "Direct Esterification of Phosphonic Acid Salts Using the Mitsunobu Reaction" *Synlett.* 6(1995):643-644.

Smee et al. "A Review of Compounds Exhibiting Anti-Orthopoxvirus Activity in Animal Models" *Antiviral Res.* 57.1-2(2003):41-52.

Smee et al. "Characterization and Treatment of Cidofovir-Resistant Vaccinia (WR Strain) Virus Infections in Cell Culture and in Mice" *Antiviral Chem. Chemother.* 16.3(2005):203-211.

Smee et al. "Effects of Four Antiviral Substances on Lethal Vaccinia Virus (IHD Strain) Respiratory Infections in Mice" *Int. I Antimicrob. Agents.* 23.5(2004):430-437.

(56) References Cited

OTHER PUBLICATIONS

Toth et al. "Hexadcyloxypropyl-Cidofovir, CMX001, Prevents Adenovirus-Induced Mortality in a Permissive, Immunosuppressed Animal Model" *PNAS.* 105.20(2008):7293-7297.

Wallot et al. "Disseminated Adenovirus Infection with Respiratory Failure in Pediatric Liver Transplant Recipients: Impact of Intravenous Cidofovir and Inhaled Nitric Oxide" *Pediatr. Transplantation.* 10(2006):121-127.

Wan et al. "Alkoxyalkyl Esters of Cidofovir and Cyclic Cidofovir: Effects of Alkyl Chain Length, Unsaturation, and Substitution on the *in vitro* Antiviral Activity in Cells Infected with HSV-1 and HCMV" *224th ACS National Meeting.* Boston, MA. Aug. 18-22, 2002. (Abstract #MEDI-30).

Wan et al. "Comparison of the Antiviral Activities of Alkoxyalkyl and Alkyl Esters of Cidofovir Against Human and Murine Cytomegalovirus Replication In Vitro" *Antimicrob. Agents Chemother.* 49.2(2005):656-662.

Wawzonek et al. "Preparation of Long Chain Alkyl Hydroperoxides" *J. Org. Chem.* 25.4(1960):621-623.

Williams-Aziz et al. "Comparative Activities of Lipid Esters of Cidofovir and Cyclic Cidofovir Against Replication of Herpesviruses In Vitro" *Antimicrob. Agents Chemother.* 49.9(2005):3724-3733.

Yang et al. "An Orally Bioavailable Antipoxvirus Compound (ST-246) Inhibits Extracellular Virus Formation and Protects Mice from Lethal Orthopoxvirus Challenge" *J. Virol.* 79.20(2005):13139-13149.

Zanger et al. "Structure-Activity Relationship and Drug Design" *Remington's Pharmaceutical Sciences.* (1980):420-435.

Zimmermann et al. "Tenofovir-Associated Acute and Chronic Kidney Disease: A Case of Multiple Drug Interactions" *Clin. Infect. Dis.* 42(2006):283-290.

\* cited by examiner

METHODS OF TREATING RETROVIRAL INFECTIONS AND RELATED DOSAGE REGIMES

RELATED APPLICATIONS

This application is a continuation application of U.S. application Ser. No. 15/044,810, filed on Feb. 16, 2016 (now allowed), which is a continuation application of U.S. application Ser. No. 13/642,985, filed on Nov. 30, 2012 (now U.S. Pat. No. 9,278,135) which is a national stage application, filed under 35 U.S.C. § 371, of International Application No. PCT/US2011/033979, filed on Apr. 26, 2011, which claims the benefit of U.S. Provisional Application No. 61/381,356, filed Sep. 9, 2010; U.S. Provisional Application No. 61/405,084, filed Oct. 20, 2010; U.S. Provisional Application No. 61/413,079, filed Nov. 12, 2010; U.S. Provisional Application No. 61/333,607, filed May 11, 2010; U.S. Provisional Application No. 61/328,491, filed Apr. 27, 2010, U.S. Provisional Application No. 61/327,919, filed Apr. 26, 2010 and U.S. Provisional Application No. 61/327,914, filed Apr. 26, 2010, each of which is incorporated by reference herein in its entirety.

FIELD OF THE INVENTION

The present invention concerns methods of treating an infection with a phosphonate ester of tenofovir.

BACKGROUND OF THE INVENTION

Human immunodeficiency virus type 1 (HIV-1) encodes three enzymes which are required for viral replication: reverse transcriptase, protease, and integrase. Combination therapy with protease inhibitors and reverse transcriptase inhibitors has a long record of effectively treating HIV and integrase inhibitors are starting to make significant contributions (See Palella, et al, N. Engl. J. Med., 338, 853-860 (1998); Richman, Nature, 410, 995-1001(2001)). However, therapy frequently fails due to the development of drug resistance, non-compliance with complicated dosing regimens, pharmacokinetic interactions, toxicity, and/or lack of potency.

3-(hexadecyloxy)propyl hydrogen ((R)-1-(6-amino-9H-purin 9-yl) propan-2-yloxy)methylphosphonate; (referred to as CMX157, hexadecyloxypropyl tenofovir or HDP-TFV), a lipid conjugate of tenofovir, was designed to mimic lysophosphatidylcholine to take advantage of natural lipid uptake pathways and to achieve high intracellular concentrations of the active antiviral, with the aim of increasing the effectiveness of tenofovir (TFV) against wild-type and mutant HIV (See Hostetler et al., Biochem Pharmacol 53:1815-22 (1997); Painter et al., Antimicrob. Agents Chemother. 51:3505-9 (2007), Lanier et al., AAC 2010, and Painter, et al., Trends Biotechnol. 22:423-7 (2004).) In addition, CMX157 may also be used to treat HIV and inhibit the development of resistance to other antiviral compounds. (See PCT Publication Nos. WO 2009/094191 and WO 2009/094190). The structure of CMX157 is shown below:

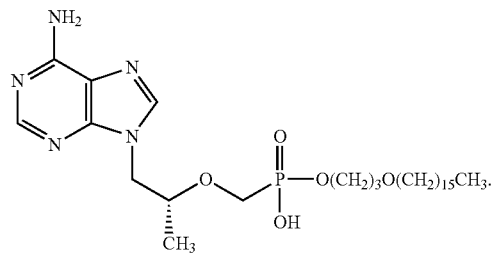

SUMMARY OF THE INVENTION

A first aspect of the invention provides the compound having the structure of formula I:

Formula I

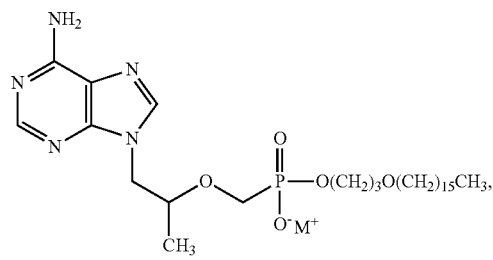

wherein $M^+$ is potassium ($K^+$), sodium ($Na^+$), lithium ($Li^+$), calcium ($Ca^{2+}$), magnesium ($Mg^{2+}$), or any pharmaceutically acceptable cation containing at least one nitrogen, or a stereoisomer, a diastereomer, an enantiomer or racemate thereof. Exemplary cations containing at least one nitrogen include, but are not limited to, various ammonium, mono, di, tri or tetra substituted amino cations. In one embodiment, the cations containing at least one nitrogen may be represented by the formula of $[NR_1R_2R_3R_4]^+$ and $R_1$, $R_2$, $R_3$, and $R_4$ are independently hydrogen or aliphatic moiety. In one embodiment, the aliphatic moiety is selected from $C_{1-5}$ alkyl (e.g., $NH_4^+$, $NH_3CH_3^+$, $NH_3CH_2CH_3^+$, etc), $C_{2-5}$ alkenyl, or $C_{2-5}$ alkynyl, etc. In another embodiment, the compound of Formula I is a salt selected from the group consisting of: methylamine, ethylamine, ethanolamine, tris(hydroxymethyl)aminomethane, ethylenediamine, dimethylamine, diethylamine, diisopropylamine, dibutylamine, di-sec-butylamine, dicyclohexylamine, diethanolamine, meglumine, pyrrolidine, piperidine, piperazine, benzathine, trimethylamine, triethylamine, triethanolamine, 1-(2-hydroxyethyl)-pyrrolidine, choline, tetra-methylammonium, and tetraethylammonium.

In one embodiment, the compound has the structure of:

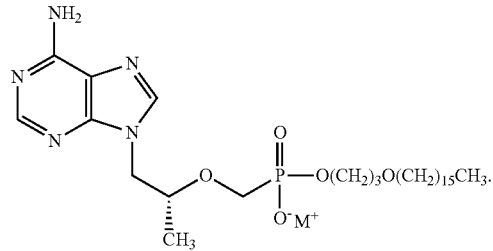

In another embodiment, M⁺ is K⁺.

Another aspect of the invention provides a pharmaceutical composition, wherein said composition is in the dosage form of a tablet or a capsule, an intravenous formulation, a solution, or a suspension comprising a compound described herein.

A further aspect of the invention provides processes of preparing a compound described herein. The processes comprise dissolving compound I in a solvent, Compound I

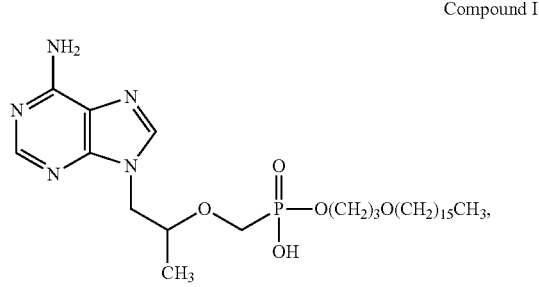

adding a base to the mixture of the solvent and compound I, and removing the solvent.

Another aspect of the invention provides methods of treating or preventing a viral disease. The methods comprises administering to a subject an effective amount of a compound described herein. In one embodiment, the virus is a retrovirus, e.g., human immunodeficiency virus (HIV) or xenotropic murine leukemia virus-related virus (XMRV). In another embodiment, the virus is Hepatitis B virus (HBV).

A further aspect of the invention provides methods of treating a subject infected with at least one retrovirus and the subject has not been administered an antiviral active agent for the retrovirus. A further aspect of the invention provides methods of treating a subject infected with HBV and the subject has not been administered an antiviral active agent for HBV. The methods comprise administering a compound described herein to the infected subject in an amount effective to treat the viral infection and inhibit the development of resistance to an antiviral compound.

Another aspect of the invention provides methods of treating a subject infected with at least one retrovirus and the subject has developed resistance or a toxic response to at least one other antiviral compound in response to prior administration of said at least one other antiviral compound to said subject for the retrovirus infection. Another aspect of the invention provides methods of treating a subject infected with HBV and the subject has developed resistance or a toxic response to at least one other anti-HBV compound in response to prior administration of said at least one other anti-HBV compound to said subject for the HBV infection. The methods comprise administering to the infected subject a compound described herein in an amount effective to treat the viral infection and inhibit the further development of resistance to an antiviral compound described herein in the infected subject.

A further aspect of the invention provides methods of inhibiting sexual transmission of HIV. The methods comprise topically applying to the skin or epithelial tissue of a human a therapeutically effective amount of a composition comprising the compound described herein. The methods further comprise concurrently administering the subject one or more additional antiviral active agents with the compound described herein.

Another aspect of the invention provides a pharmaceutical composition comprising the compound described herein and at least one additional antiviral active agent and a pharmaceutically acceptable carrier.

Preferably the compound of the invention is administered orally, preferably at a dosage of from about 1 mg/kg to about 100 mg/kg, more preferably at a dosage of from about 1 mg/kg to about 20 mg/kg. For example, said compound is administered to said subject at a dosage of 1, 2, 3, 4, 5, 6, 7, 8, 9, 10, 11, 12, 13, 14, 15, 16, 17, 18, 19 or 20 mg/kg. In addition, said compound is administered to said subject in an amount of about 25, 50, 75, 100, 125, 150, 175, 200, 250, 300, 350, 400, 450, 500, 600, 700, 800, 900, 1000, 1100, 1200, 1300, 1400, 1500, 1600, 1700, 1800, 1900 or 2000 mg. The compounds of the invention can be administered, for example, as a single dose, daily, or weekly.

In one embodiment, the compound which is orally administered is:

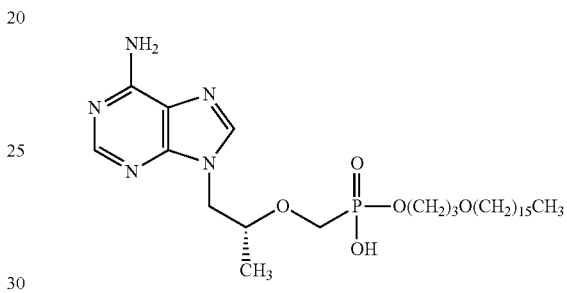

or a pharmaceutically acceptable salt thereof.

With respect to disorders associated with viral infections, the "effective amount" is determined with reference to the recommended dosages of the antiviral compound. The selected dosage will vary depending on the activity of the selected compound, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient will depend on a variety of factors, including the body weight, general health, diet, time, and route of administration and combination with other drugs, and the severity of the disease being treated.

The compounds of the invention can be administered, for example, once per day for 1, 2, 3, 4, 5, 6, 7, 8, 9, or 10 days or more. For example, 25 mg of a compound of the invention can be administered daily. For example, 50 mg of a compound of the invention can be administered daily. For example, 100 mg of a compound of the invention can be administered daily. For example, 150 mg of a compound of the invention can be administered daily. For example, 200 mg of a compound of the invention can be administered daily. For example, 400 mg of a compound of the invention can be administered daily.

The compounds of the invention can be administered, for example, once per week for 1, 2, 3, 4, 5, 6, 7, 8, 9, or 10 weeks or more. For example, 25 mg of a compound of the invention can be administered weekly. For example, 50 mg of a compound of the invention can be administered weekly. For example, 100 mg of a compound of the invention can be administered weekly. For example, 150 mg of a compound of the invention can be administered weekly. For example, 200 mg of a compound of the invention can be administered weekly. For example, 250 mg of a compound of the invention can be administered weekly. For example, 300 mg of a compound of the invention can be administered weekly. For example, 350 mg of a compound of the invention can be administered weekly. For example, 400 mg of a compound of the invention can be administered weekly. For example, 450 mg of a compound of the invention can be administered weekly. For example, 500 mg of a compound of the invention can be administered weekly. For example, 750 mg of a compound of the invention can be administered weekly. For example, 1000 mg of a compound of the invention can be administered weekly. For example, 1250 mg of a compound of the invention can be administered weekly. For example, 1500 mg of a compound of the invention can be administered weekly. For example, 1750 mg of a compound of the invention can be administered weekly. For example, 2000 mg of a compound of the invention can be administered weekly.

The methods of the present invention provide higher concentrations of active antiviral (i.e., tenofovir diphosphate) in vivo using lower dosages of the compound of the invention relative to tenofovir administration.

DETAILED DESCRIPTION OF THE INVENTION

Figure 1:
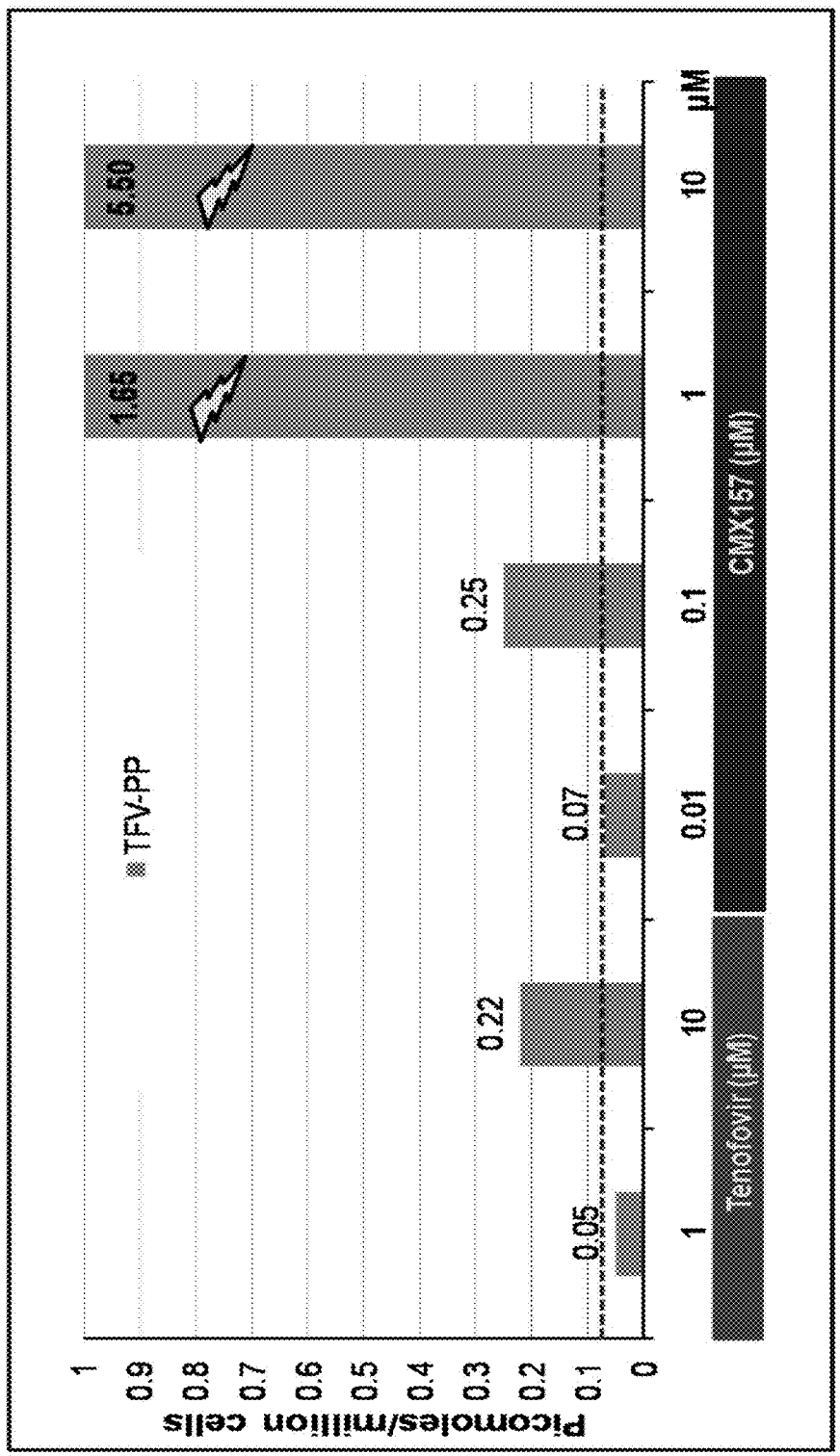
FIG. 1 depicts higher active drug levels in human PBMCs exposed to CMX157 versus tenofovir in vitro.

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

All patents, patent applications and publications referred to herein are incorporated by reference in their entirety. In case of a conflict in terminology, the present specification is controlling.

As used herein, "alkali metals" are chemical elements from Group 1 of the periodic table of elements, for example: lithium (Li), sodium (Na), and potassium (K).

Subjects to be treated by the methods of the present invention are, in general, mammalian and primate subjects (e.g., human, monkey, ape, chimpanzee). Subjects may be male or female and may be of any age, including prenatal (i.e., in utero), neonatal, infant, juvenile, adolescent, adult, and geriatric subjects. Thus, in some cases the subjects may be pregnant female subjects.

As used herein, "Human immunodeficiency virus" (or "HIV") as used herein is intended to include all subtypes thereof, including HIV subtypes A, B, C, D, E, F, G, and O, and HIV-2.

As used herein, "Hepatitis B virus" (or "HBV") as used herein is intended to include all subtypes (adw, adr, ayw, and ayr) and or genotypes (A, B, C, D, E, F, G, and H) thereof.

As used herein, "a therapeutically effective amount" refers to an amount that will provide some alleviation, mitigation, and/or decrease in at least one clinical symptom in the subject. Those skilled in the art will appreciate that the therapeutic effects need not be complete or curative, as long as some benefit is provided to the subject.

As used herein, "specificity" or "specifically against" refers to a compound that may selectively inhibit the metabolic activity and/or DNA replication of a certain type of viral infected cells. The specificity may be tested by using any methods known to one skilled in the art, for example, testing $IC_{90}$ and/or $IC_{50}$. In some embodiments, the compounds described herein may have $IC_{90}$ and/or $IC_{50}$ against viral infected cells to be at least about three fold lower than the $IC_{90}$ and/or $IC_{50}$ against normal (uninfected) cells. In some embodiments, the compounds described herein may have $IC_{90}$ and/or $IC_{50}$ against viral infected cells to be about three fold to ten fold lower than the $IC_{90}$ and/or $IC_{50}$ against normal (uninfected) cells. In some embodiments, the compounds described herein may have $IC_{90}$ and/or $IC_{50}$ against viral infected cells to be at least ten fold lower than the $IC_{90}$ and/or $IC_{50}$ against normal (uninfected) cells. In some embodiments, the compounds described herein may have specific cytotoxicity against viral infected and/or transformed cells. The cytotoxicity may be measured by any methods known to one skilled in the art.

Unless otherwise stated, structures depicted herein are meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

As used herein, the terms "treatment," "treat," and "treating" refer to reversing, alleviating, inhibiting the progress of a disease or disorder as described herein, or delaying, eliminating or reducing the incidence or onset of a disorder or disease as described herein, as compared to that which would occur in the absence of the measure taken.

In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Active compounds of the present invention may optionally be administered in combination (or in conjunction) with other active compounds and/or agents useful in the treatment of viral infections as described herein. The administration of two or more compounds "in combination" or "in conjunction" means that the two or more compounds are administered closely enough in time to have a combined effect, for example an additive and/or synergistic effect. The two or more compounds may be administered simultaneously (concurrently) or sequentially or it may be two or more events occurring within a short time period before or after each other. Simultaneous administration may be carried out by mixing the compounds prior to administration, or by administering the compounds at the same point in time but at different anatomic sites or using different routes of administration. In some embodiments, the other antiviral agent(s) may optionally be administered concurrently.

"Parenteral" as used herein refers to subcutaneous, intravenous, intra-arterial, intramuscular or intravitreal injection, or infusion techniques.

"Topically" as used herein encompasses administration rectally and by inhalation spray, as well as the more common routes of the skin and mucous membranes of the mouth and nose and in toothpaste.

One aspect of the invention provides a compound of formula I:

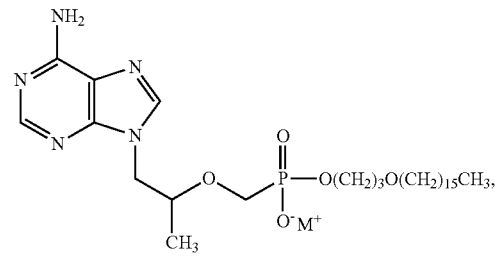

Formula I wherein $M^+$ is potassium ($K^+$), sodium ($Na^+$), lithium ($Li^+$), calcium ($Ca^{2+}$), magnesium ($Mg^{2+}$), or any pharmaceutically acceptable cation containing at least one nitrogen, or a stereoisomer, diastereomer, enantiomer or racemate thereof. Exemplary cations containing at least one nitrogen include, but are not limited to, various ammonium, mono, di, tri or tetra substituted amino cations. In one embodiment, the cations containing at least one nitrogen may be represented by the formula of $[NR_1R_2R_3R_4]^+$ and $R_1$, $R_2$, $R_3$, and $R_4$ are independently hydrogen or aliphatic moiety. In one embodiment, the aliphatic moiety is selected from $C_{1-5}$ alkyl (e.g., $NH_4^+$, $NH_3CH_3^+$, $NH_3CH_2CH_3^+$, etc), $C_{2-5}$ alkenyl, or $C_{2-5}$ alkynyl, etc. In another embodiment, the compound of Formula I is a salt selected from the group consisting of: methylamine, ethylamine, ethanolamine, tris(hydroxymethyl)aminomethane, ethylenediamine, dimethylamine, diethylamine, diisopropylamine, dibutylamine, di-sec-butylamine, dicyclohexylamine, diethanolamine, meglumine, pyrrolidine, piperidine, piperazine, benzathine, trimethylamine, triethylamine, triethanolamine, 1-(2-hydroxyethyl)-pyrrolidine, choline, tetra-methylammonium, and tetraethylammonium. For compounds of formula I, when $M^+$ is $Ca^{2+}$ or $Mg^{2+}$, two equivalents of the anion are present to meet the requirement for cation-anion balance.

In one embodiment, the compound has the structure of:

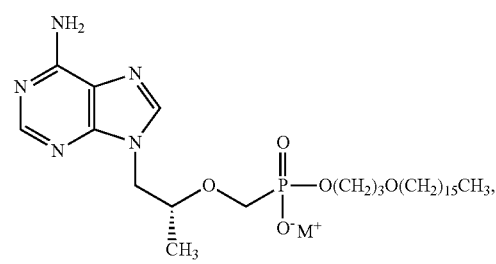

wherein $M^+$ is $K^+$.

The salt may be in various forms, all of which are included within the scope of the invention. These forms include anhydrous form or solvates. In one embodiment, M+ is K+. In other embodiments, the salt may be crystalline. In one embodiment, the compound is a potassium salt of CMX157.

In general, the compounds of this invention may be prepared by standard techniques known in the art and by known processes analogous thereto. For example, CMX157 may be prepared in accordance with known procedures, or variations thereof that will be apparent to those skilled in the art. See, e.g., Painter et al., *Antimicrobial Agents and Chemotherapy* 51, 3505-3509 (2007) and US Patent Application Publication No. 2007/0003516 to Almond et al.

General methods for preparing compounds of the present invention are set forth below. In the following description, all variables are, unless otherwise noted, as defined in the formulas described herein. The following non-limiting descriptions illustrate the general methodologies that may be used to obtain the compounds described herein.

In one embodiment, the compound described herein may be prepared by dissolving compound 1 in an appropriate solvent,

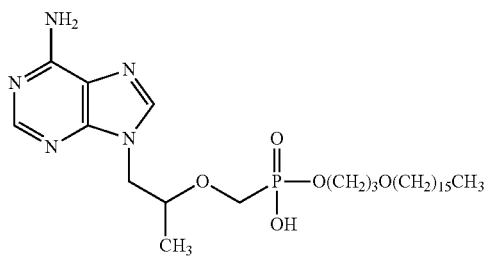

Compound 1 adding a suitable base to the mixture of the solvent and compound 1, and removing the solvent to provide the compound of formula I.

The solvent used in the preparation may be any suitable solvent known to one skilled in the art or a combination of solvents that provides satisfactory yield of the product. In one embodiment, the solvent is a mixture of at least two solvents. Exemplary combination of solvents includes, but is not limited to, dichloromethane and methanol, dichloromethane and ethanol. In one embodiment, the molar ratio of the dichloromethane and methanol is in a range of about 1:1 to 9:1. In one embodiment, the molar ratio of the dichloromethane and methanol is in a range of about 7:3 to 9:1. In a further embodiment, the molar ratio of the dichloromethane and methanol is about 9:1.

The base used in the preparation may be any suitable base known to one skilled in the art or a combination of bases that provides satisfactory yield of the product. In some embodiments, the base is an alkali metal alcoholate base. Exemplary bases include, but are not limited to, potassium methoxide, sodium methoxide, lithium tert-butoxide, ammonium hydroxide, sodium hydroxide, potassium hydroxide, and lithium hydroxide.

The process described herein may further include the step of recrystallization to remove impurity, side products, and unreacted starting material. The recrystallization step comprises the step of dissolving the product in a suitable solvent at an appropriate temperature, cooling to an appropriate temperature for a sufficient period of time to precipitate the compound, and filtering to provide the compound of formula I. In some embodiments, the temperature for the step of dissolving is in a range of about 50° C. to 80° C.

Additional antiviral active agents that may be used in carrying out the present invention include HIV-protease inhibitors, nucleoside reverse transcriptase inhibitors (this term herein including nucleotide reverse transcriptase inhibitors), non-nucleoside reverse transcriptase inhibitors, integrase inhibitors, entry inhibitors, fusion inhibitors, maturation inhibitors, and combinations thereof. Numerous examples are known and described in, for example, US Patent Application Publication No. 2006/0234982 to Dahl et al. at Table A therein, and in Table 1 as set forth below.

Additional antiviral active agents that may be used in carrying out the present invention include ribavirin, interferon (e.g., interferon alpha, pegylated interferon), lamivudine, entecavir, telbivudine, emtricitabine, clevudine, BAM-205 (NOV-205), LB80380, MIV-210 (lagociclovir valactate), simvastatin, Bay 41-4109 and combinations thereof.

Additional examples include, but are not limited to, the integrase inhibitor Isentress or raltegravir (MK-0518: Merck), the CCR5 inhibitor Maraviroc or selzentry (and K-427857, Pfizer) and others of these classes.

Additional examples are provided in U.S. Pat. No. 7,094,413 to Buelow et al.; U.S. Pat. No. 7,250,421 to Nair et al., US Patent Application Publication No. 2007/0265227 to Heneine et al. and US Patent Application Publication No. 2007/0072831 to Cai et al.

The non-nucleoside reverse transcriptase inhibitor ("NNRTI") 6-chloro-4-cyclopropylethynyl-4-trifluoromethyl-1,4-dihydro-2H3,1-benzoxazin-2-one, and pharmaceutically acceptable salts thereof, are described in, for example, U.S. Pat. No. 5,519,021. Examples of the present invention include efavirenz.

The nucleoside reverse transcriptase inhibitor ("NRTI") 2-hydroxymethyl-5-(5-fluorocytosin-1-yl)-1, 3-oxathiolane ("FTC") and pharmaceutically acceptable salts thereof, are described in, for example, U.S. Pat. No. 6,642,245 to Liotta et al. Examples of the present invention include emtricitabine.

Integrase inhibitors include, but are not limited to, those described in US Patent Application Publication No. 2007/0072831, WO 02/30426, WO 02/30930, WO 02/30931, WO 02/055079, WO 02/36734, U.S. Pat. No. 6,395,743; U.S. Pat. No. 6,245,806; U.S. Pat. No. 6,271,402; WO 00/039086; WO 00/075122; WO 99/62513; WO 99/62520; WO 01/00578; Jing, et al., Biochemistry, 41, 5397-5403, (2002); Pais, et al., J. Med. Chem., 45, 3184-94 (2002); Goldgur, et al., Proc. Natl. Acad. Sci. U.S.A., 96, 13040-13043 (1999); Espeseth, et al., Proc. Natl. Acad. Sci. U.S.A., 97, 11244-11249, (2000); WO 2005/016927, WO 2004/096807, WO 2004/035577, WO 2004/035576 and US 2003/0055071.

TABLE 1

Additional Antiviral Agents 5,6 dihydro-5-azacytidine
5-aza 2'deoxycytidine
5-azacytidine
5-yl-carbocyclic 2'-deoxyguanosine (BMS200,475)
9-(arabinofuranosyl)guanine; 9-(2'-deoxyribofuranosyl)guanine
9-(2'-deoxy-2'-fluororibofuranosyl)-2,6-diaminopurine
9-(2'-deoxy-2'-fluororibofuranosyl)guanine
9-(2'-deoxyribofuranosyl)-2,6-diaminopurine
9-(arabinofuranosyl)-2,6-diaminopurine TABLE 1-continued Additional Antiviral Agents Abacavir, ZIAGEN ®
Acyclovir, ACV; 9-(2-hydroxyethoxylmethyl)guanine
Adefovir dipivoxil, HEPSERA ®
Amdoxivir, DAPD
Amprenavir, AGENERASE ®
araA; 9-β-D-arabinofuranosyladenine (Vidarabine)
Atazanivir sulfate (REYATAZ ®)
AZT; 3'-azido-2',3'-dideoxythymdine, Zidovudine, (RETROVIR ®)
BHCG;(+−)-(1a,2b,3a)-9-[2,3-bis(hydroxymethyl)cyclobutyl]guanine
BMS200,475; 5-yl-carbocyclic 2'-deoxyguanosine
Buciclovir; (R) 9-(3,4-dihydroxybutyl)guanine
BvaraU; 1-β-D-arabinofuranosyl-E-5-(2-bromovinyl)uracil (Sorivudine)
Calanolide A
Capravirine
CDG; carbocyclic 2'-deoxyguanosine
Cidofovir, HPMPC; (S)-9-(3-hydroxy-2-phosphonylmethoxypropyl)cytosine
Clevudine, L-FMAU; 2'-Fluoro-5-methyl-β-L-arabino-furanosyluracil
COMBIVIR ® (lamivudine/zidovudine)
Cytallene; [1-(4'-hydroxy-1',2'-butadienyl)cytosine]
DAPD; (−)-β-D-2,6-diaminopurine dioxolane
ddA; 2',3'-dideoxyadenosine
ddAPR; 2,6-diaminopurine-2',3'-dideoxyriboside
ddC; 2',3'-dideoxycytidine (Zalcitabine)
ddI; 2',3'-dideoxyinosine, didanosine, (VIDEX ®, VIDEX ® EC)
Delavirdine, RESCRIPTOR ®
Didanosine, ddI, VIDEX ®; 2',3'-dideoxyinosine
DXG; dioxolane guanosine
E-5-(2-bromovinyl)-2'-deoxyuridine
Efavirenz, SUSTIVA ®
Enfuvirtide, FUZEON ®
F-ara-A; fluoroarabinosyladenosine (Fludarabine)
FDOC; (−)-β-D-5-fluoro-1-[2-(hydroxymethyl)-1,3-dioxolane]cytosine
FEAU; 2'-deoxy-2'-fluoro-1-β-D-arabinofuranosyl-5-ethyluracil
FIAC; 1-(2-deoxy-2-fluoro-β-D-ababinofuranosyl)-5-iodocytosine
FIAU; 1-(2-deoxy-2-fluoro-β-D-ababinofuranosyl(-5-iodouridine
FLG; 2',3'-dideoxy-3'-fluoroguanosine
FLT; 3'-deoxy-3'-fluorothymidine
Fludarabine; F-ara-A; fluoroarabinosyladenosine
FMAU; 2'-Fluoro-5-methyl-β-L-arabino-furanosyluracil
FMdC
Foscarnet; phosphonoformic acid, PFA
FPMPA; 9-(3-fluoro-2-phosphonylmethoxypropyl)adenine
Gancyclovir, GCV; 9-(1,3-dihydroxy-2-propoxymethyl)guanine
GS-7340; 9-[R-2-[[(S)-[[(S)-1-(isopropoxycarbonyl)ethyl]amino]-phenoxyphosphinyl methoxy]propyl]adenine
HPMPA; (S)-9-(3-hydroxy-2-phosphonylmethoxypropyl)adenine
HPMPC; (S)-9-(3-hydroxy-2-phosphonylmethoxypropyl)cytosine (Cidofovir)
Hydroxyurea, DROXIA ®
Indinavir, CRIXIVAN ®
KALETRA ® (lopinavir/ritonavir)
Lamivudine, 3TC, EPIVIR ™; (2R,5S,cis)-4-amino-1-(2-hydroxymethyl-1,3-oxathiolan-5-yl)-(1H)-pyrimidin-2-one
L-d4C; L-3'-deoxy-2',3'-didehydrocytidine
L-ddC; L-2',3'-dideoxycytidine
L-Fd4C; L-3'-deoxy-2',3'-didehydro-5-fluorocytidine
L-FddC; L-2',3'-dideoxy-5-fluorocytidine
Lopinavir
Nelfinavir, VIRACEPT ®
Nevirapine, VIRAMUNE ®
Oxetanocin A; 9-(2-deoxy-2-hydroxymethyl-β-D-erythro-oxetanosyl)adenine
OxetanocinG; 9-(2-deoxy-2-hydroxymethyl-β-D-erythro-oxetanosyl)guanine
Penciclovir
PMEDAP; 9-(2-phosphonylmethoxyethyl)-2,6-diaminopurine
PMPA, tenofovir; (R)-9-(2-phosphonylmethoxypropyl)adenine
PPA; phosphonoacetic acid
Ribavirin; 1-β-D-ribofuranosyl-1,2,4-triazole-3-carboxamide
Ritonavir, NORVIR ®
Saquinavir, INVIRASE ®, FORTOVASE ®
Sorivudine, BvaraU; 1-β-D-arabinofuranosyl-E-5-(2-bromovinyl)uracil
Stavudine, d4T, ZERIT ®; 2',3'-didehydro-3'-deoxythymidine
Trifluorothymidine, TFT;
TRIZIVIR ® (abacavir sulfate/lamivudine/zidovudine)
Vidarabine, araA; 9-β-D-arabinofuranosyladenine
VIREAD ®, tenofovir disoproxil fumarate (DF), Bis POC PMPA, TDF;

TABLE 1-continued

Additional Antiviral Agents 2,4,6,8-Tetraoxa-5-phosphanonanedioic acid, 5-[[(1R)-2-(6-amino-9H-purin-9-yl)-1-methylethoxy]methyl]-, bis(1-methylethyl)ester, 5-oxide, (2E)-2-butenedioate (1:1)
Zalcitabine, HIVID ®, ddC; 2',3'0dideoxycytidine
Zidovudine, AZT, RETROVIR ®; 3'-azido-2',3'-dideoxythymidine
Zonavir; 5-propynyl-1-arabinosyluracil
Rilpivirine (TMC278)

In another embodiment, the compositions of the present invention can include an active compound as described herein in combination with one or more (e.g., 1, 2, 3) additional active agents described above, in analogous manner as known in the art. For example, combinations of efavirenz (an NNRTI), emtricitabine (an NRTI) and tenofovir DF (an NRTI) are described in, for example, Dahl et al., US Patent Application Publication No. 2007/0099902 to Dahl et al. Specific examples of such combinations include, but are not limited to: a compound described herein in combination with:

(a) FTC/Efavirenz;
(b) 3TC/Efavirenz;
(c) AZT/3TC;
(d) FTC;
(e) 3TC;
(f) FTC/Isentress;
(g) 3TC/Isentress;
(h) PPL-100;
(i) FTC/TMC278;
(j) 3TC/TMC278;
(k) FTC/TMC125; or
(l) 3TC/TMC125.

In one embodiment, the present invention is a pharmaceutical composition comprising a compound described herein. In another embodiment, the pharmaceutical composition further comprises a pharmaceutically acceptable carrier. The term "pharmaceutically acceptable carrier" as used herein refers to any substance, not itself a therapeutic agent, used as a vehicle for delivery of a therapeutic agent to a subject. Examples of pharmaceutically acceptable carriers and methods of manufacture for various compositions include, but are not limited to, those described in Remington's Pharmaceutical Sciences, 18th Ed., Mack Publishing Co. (1990) (See also US Patent Application US 2007/0072831).

The compounds of the invention may be formulated with conventional carriers, diluents and excipients, which will be selected in accord with ordinary practice. Tablets will contain excipients, glidants, fillers, binders, diluents and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Compounds of the invention (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferably to present them as pharmaceutical formulations. The formulations, both for veterinary and for human use, of the present invention comprise at least one active ingredient, as above defined, together with one or more pharmaceutically acceptable carriers (excipients, diluents, etc.) thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are, in some embodiments, applied as a topical ointment or cream containing the active ingredient(s) in an amount of, for example, 0.005 to 20% w/w (including active ingredient(s) in a range between 0.05% and 20% in increments of 0.05% w/w such as 0.6% w/w, 0.65% w/w, 0.7% w/w, etc), in some embodiments, 0.05 to 15% w/w and in other embodiments, 0.05 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. In some embodiments, a hydrophilic emulsifier is included together with a lipophilic emulsifier which acts as a stabilizer. In some embodiments, it includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the present invention include TWEEN®60, SPAN®80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. In some embodiments, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. In some embodiments, the active ingredient is present in such formulations in a concentration of 0.1 to 20%. In some embodiments, the active ingredient is present in a concentration of 0.1 to 10%. In some embodiments, the active ingredient is present in a concentration of about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, rings, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds described herein may be used to provide controlled release pharmaceutical formulations containing as active ingredient one or more compounds of the invention ("controlled release formulations") in which the release of the active ingredient can be controlled and regulated to allow less frequent dosing or to improve the pharmacokinetic or toxicity profile of a given invention compound. Controlled release formulations adapted for oral administration in which discrete units comprising one or more compounds of the invention can be prepared according to conventional methods. Controlled release formulations may be employed for the treatment or prophylaxis of various microbial infections particularly human bacterial, human parasitic protozoan or human viral infections caused by microbial species including Plasmodium, Pneumocystis, herpes viruses (CMV, HSV 1, HSV 2, VZV, and the like), retroviruses, adenoviruses and the like. The controlled release formulations can be used to treat HIV infections and related conditions such as tuberculosis, malaria, pneumocystis pneumonia, CMV retinitis, AIDS, AIDS-related complex (ARC) and progressive generalized lymphadeopathy (PGL), and AIDS-related neurological conditions such as multiple sclerosis, and tropical spastic paraparesis. Other human retroviral infections that may be treated with the controlled release formulations according to the invention include Human T-cell Lymphotropic virus and HIV-2 infections. The invention accordingly provides pharmaceutical formulations for use in the treatment or prophylaxis of the above-mentioned human or veterinary conditions and microbial infections.

Pharmacokinetic Enhancers.

The compounds described herein may be employed in combination with pharmacokinetic enhancers (sometimes also referred to as "booster agents"). One aspect of the invention provides the use of an effective amount of an enhancer to enhance or "boost" the pharmacokinetics of a compound of the invention. An effective amount of an enhancer, for example, the amount required to enhance an active compound or additional active compound of the invention, is the amount necessary to improve the pharmacokinetic profile or activity of the compound when compared to its profile when used alone. The compound possesses a better efficacious pharmacokinetic profile than it would without the addition of the enhancer. The amount of pharmacokinetic enhancer used to enhance the potency of the compound is, preferably, subtherapeutic (e.g., dosages below the amount of booster agent conventionally used for therapeutically treating infection in a patient). An enhancing dose for the compounds of the invention is subtherapeutic for treating infection, yet high enough to effect modulation of the metabolism of the compounds of the invention, such that their exposure in a patient is boosted by increased bioavailability, increased blood levels, increased half life, increased time to peak plasma concentration, increased/faster inhibition of HIV integrase, RT or protease and/or reduced systematic clearance. One example of a pharmacokinetic enhancer is RITONAVIR™ (Abbott Laboratories).

In accordance with one aspect of the invention, there are provided methods for treating disorders caused by viral infections. In some aspects of the invention, the virus is a retrovirus. In one embodiment, the virus is a gamma retrovirus. As used herein, "retrovirus" is an RNA virus that is replicated in a host cell via the enzyme reverse transcriptase to produce DNA from its RNA genome. The DNA is then incorporated into the host's genome by an integrase enzyme. The virus thereafter replicates as part of the host cell's DNA. Retroviruses are enveloped viruses that belong to the viral family Retroviridae. Exemplary retroviruses include, but are not limited to, human immunodeficiency virus (HIV) and xenotropic murine leukemia virus-related virus (XMRV). In addition, there is evidence to indicate that XMRV may be related to chronic fatigue syndrome (CFS). (See, e.g., Lombardi, et al., Science, vol. 326, P 585-589 (October 2009).)

In another embodiment, the invention provides a method of treating or preventing an XMRV infection comprising administering to a subject an effective amount of a compound of the invention. In another embodiment, the invention provides a method of treating or preventing chronic fatigue syndrome comprising administering to a subject an effective amount of a compound of the invention. In another embodiment, the invention provides a method of treating or preventing prostate cancer comprising administering to a subject an effective amount of a compound of the invention.

In another embodiment, the invention provides a method of treating or preventing a hepatitis B infection comprising administering to a subject an effective amount of a compound of the invention.

In one embodiment, the subject is human. In one embodiment, the subject is an immunocompromised and/or an immunosuppressed subject. In some embodiments, the toxic side effects in the immunodeficient subject are decreased when using the methods of the present invention, compared to the toxic side effects of using tenofovir or other antiviral agents.

As used herein, immunodeficiency (or immune deficiency) is a state in which the immune system's ability to fight infectious disease is compromised or entirely absent. An immunocompromised subject is a subject that has an immunodeficiency of any kind or of any level. Exemplary immunocompromised subject includes, but are not limited to, a subject with primary immunodeficiency (a subject that is born with defects in immune system) and a subject with secondary (acquired) immunodeficiency In addition, other common causes for secondary immunodeficiency include, but are not limited to, malnutrition, aging and particular medications (e.g. immunosuppressive therapy, such as chemotherapy, disease-modifying antirheumatic drugs, immunosuppressive drugs after organ transplants, glucocorticoids). Other exemplary diseases that directly or indirectly impair the immune system include, but are not limited to, various types of cancer, (e.g. bone marrow and blood cells (leukemia, lymphoma, multiple myeloma)), acquired immunodeficiency syndrome (AIDS) caused by human immunodeficiency virus (HIV), chronic infections and autoimmune diseases (e.g. Acute disseminated encephalomyelitis (ADEM), Addison's disease, Alopecia areata, Ankylosing spondylitis, Antiphospholipid antibody syndrome (APS), Autoimmune hemolytic anemia, Autoimmune hepatitis, Autoimmune inner ear disease, Bullous pemphigoid, Coeliac disease, Chagas disease, Chronic obstructive pulmonary disease, Crohns Disease, Dermatomyositis, Diabetes mellitus type 1, Endometriosis, Goodpasture's syndrome, Graves' disease, Guillain-Barré syndrome (GBS), Hashimoto's disease, Hidradenitis suppurativa, Kawasaki disease, IgA nephropathy, Idiopathic thrombocytopenic purpura, Interstitial cystitis, Lupus erythematosus, Mixed Connective Tissue Disease, Morphea, Multiple sclerosis (MS), Myasthenia gravis, Narcolepsy, Neuromyotonia, Pemphigus vulgaris, Pernicious anaemia, Psoriasis, Psoriatic Arthritis, Polymyositis, Primary biliary cirrhosis, Rheumatoid arthritis, Schizophrenia, Scleroderma, Sjögren's syndrome, Stiff person syndrome, Temporal arteritis (also known as "giant cell arteritis"), Ulcerative Colitis, Vasculitis, Vitiligo, Wegener's granulomatosis.)

The antiviral activity for CMX157 has been described in U.S. Pat. Nos. 6,716,825, 7,034,014, 7,094,772, 7,098,197, 7,452,898, and PCT publication No. WO 2008/133966, which are incorporated by references in their entireties.

It has also been found that compounds described herein may associate or bind to viral particles. Since viral particles migrate or permeate into cellular or tissue compartments that are not generally accessible to active therapeutic agents (thus creating a substantially untreated "reservoir" of infection when subjects are systemically administered such agents), this finding makes possible (a) the treatment of infection in such privileged compartments, and (b) the use of active agents in prophylactic or microbicidal treatments (where association or binding of the active agent to virus before infection occurs is of therapeutic benefit).

In general, a privileged compartment is a cellular or tissue compartment to which said virus permeates in vivo, to which said active agent does not efficiently permeate in vivo in the absence of said virus, and to which said active agent is carried in vivo by said virus when said active agent binds to said virus. For example, when the privileged compartment is a tissue compartment, it may be brain (central nervous system), lymphoid, or testes. Examples of cellular privileged compartments include but are not limited to dendritic cells, microglia, monocyte/macrophages, and combinations thereof. Compositions and methods of treating privileged compartment infections may be prepared and carried out as described above. Prophylactic compositions, devices and methods are discussed in further detail below.

The treatment for privileged compartment infections using CMX157 has been described in PCT Publication Nos. WO 2009/094191 and WO 2009/094190, which are incorporated by references in their entireties.

The present invention can take the form of a topical compositions containing the active agents described herein for inhibiting or combating viral infection, e.g., for prophylactic use. Such compositions (with active agents other than those disclosed herein) are known and described in, for example, U.S. Pat. No. 6,545,007, the disclosure of which is incorporated herein by reference in its entirety.

Such compositions can take several forms. Thus, in one embodiment, the composition is in the form of a cream, lotion, gel, or foam that is applied to the affected skin or epithelial cavity, and preferably spread over the entire skin or epithelial surface which is at risk of contact with bodily fluids. Such formulations, which are suitable for vaginal or rectal administration, may be present as aqueous or oily suspensions, solutions or emulsions (liquid formulations) containing in addition to the active ingredient, such carriers as are known in the art to be appropriate. For "stand-alone" lubricants (i.e., lubricants that are not pre-packaged with condoms), gels and similar aqueous formulations are generally preferred, for various reasons (both scientific and economic) known to those skilled in the art. These formulations are useful to protect not only against sexual transmission of HIV, but also to prevent infection of a baby during passage through the birth canal. Thus the vaginal administration can take place prior to sexual intercourse, during sexual intercourse, and immediately prior to childbirth.

One method of applying an antiviral lubricant to the genitals, for the purposes disclosed herein, involves removing a small quantity (such as a teaspoon, or several milliliters) of a gel, cream, ointment, emulsion, or similar formulation from a plastic or metallic tube, jar, or similar container, or from a sealed plastic, metallic or other packet containing a single dose of such composition, and spreading the composition across the surface of the penis immediately before intercourse. Alternate methods of emplacement include: (1) spreading the composition upon accessible surfaces inside the vagina or rectum shortly before intercourse; and (2) emplacing a condom, diaphragm, or similar device, which has already been coated or otherwise contacted with an anti-viral lubricant, upon the penis or inside the vagina. In a preferred embodiment, any of these methods of spreading an anti-viral lubricant across the surfaces of the genitals causes the lubricant to coat and remain in contact with the genital and epithelial surfaces throughout intercourse.

In one embodiment the compositions are used in conjunction with condoms, to enhance the risk-reducing effectiveness of condoms and provide maximum protection for users. The composition can either be coated onto condoms during manufacture, and enclosed within conventional watertight plastic or foil packages that contain one condom per package, or it can be manually applied by a user to either the inside or the outside of a condom, immediately before use.

As used herein, "condom" refers to a barrier device which is used to provide a watertight physical barrier between male and female genitalia during sexual intercourse, and which is removed after intercourse. This term includes conventional condoms that cover the penis; it also includes so-called "female condoms" which are inserted into the vaginal cavity prior to intercourse. The term "condom" does not include diaphragms, cervical caps or other barrier devices that cover only a portion of the epithelial membranes inside the vaginal cavity. Preferably, condoms should be made of latex or a synthetic plastic material such as polyurethane, since these provide a high degree of protection against viruses.

In another embodiment the composition is in the form of an intra-vaginal pill, an intra-rectal pill, or a suppository. The suppository or pill should be inserted into the vaginal or rectal cavity in a manner that permits the suppository or pill, as it dissolves or erodes, to coat the vaginal or rectal walls with a prophylactic layer of the anti-HIV agent.

In still another embodiment the composition is topically applied by release from an intravaginal device. Devices such as vaginal rings, vaginal sponges, diaphragms, cervical caps, female condoms, and the like can be readily adapted to release the composition into the vaginal cavity after insertion.

Compositions used in the methods of this invention may also comprise additional active agents, such as another agent(s) to prevent HIV infection, and agents that protect individuals from conception and other sexually transmitted diseases. Thus, in another embodiment, the compositions used in this invention further comprise one or more additional anti-HIV agents, virucides effective against viral infections other than HIV, and/or spermicides.

In one particular embodiment, the composition contains nonoxynol, a widely-used spermicidal surfactant. The resulting composition could be regarded as a "bi-functional" composition, since it would have two active agents that provide two different desired functions, in a relatively inert carrier liquid; the nonoxynol would provide a spermicidal contraceptive agent, and the compound of the invention (i.e., CMX157 or a pharmaceutically acceptable salt thereof) would provide anti-viral properties. The nonoxynol is likely to cause some level of irritation, in at least some users; this is a well-known side effect of spermicidal surfactants such as nonoxynol and octoxynol, which attack and destroy the lipid bilayer membranes that surround sperm cells and other mammalian cells.

The compositions used in this invention may also contain a lubricant that facilitates application of the composition to the desired areas of skin and epithelial tissue, and reduces friction during sexual intercourse. In the case of a pill or suppository, the lubricant can be applied to the exterior of the dosage form to facilitate insertion.

In still another embodiment the invention provides a device for inhibiting the sexual transmission of HIV comprising (a) a barrier structure for insertion into the vaginal cavity, and (b) a composition comprising an active agent as described herein. As mentioned above, preferred devices which act as barrier structures, and which can be adapted to apply anti-HIV agent, include the vaginal sponge, diaphragm, cervical cap, or condom (male or female).

The methods, compositions and devices of this invention can be adapted generally to release active agent in a time sensitive manner that best corresponds to the timing of sexual activity. When topically applied as a lotion or gel, the compositions are preferably applied immediately prior to sexual activity. Other modes of application, such as devices and suppositories, can be designed to release active agent over a prolonged period of time, at a predetermined rate, depending upon the needs of the consumer.

The topical compositions and microbicidal methods using CMX157 have also been described in PCT Publication Nos. WO 2009/094191 and WO 2009/094190, which are incorporated by references in their entireties.

The present invention will now be described in more detail with reference to the following examples. However, these examples are given for the purpose of illustration and are not to be construed as limiting the scope of the invention.

EXAMPLES

Example 1

Anti-HIV Evaluation for CMX157

The following example demonstrates the results of in vitro anti-HIV-1 evaluations of CMX157 in parallel with AZT. The experimental details and results are discussed below.

1. Compounds

The activity of CMX157 against HIV was previously tested. Specifically, CMX157 $IC_{50}$s against HIV-1 subtypes (A-G, O) ranged from <1 to 7 nM. In comparison, tenofovir $IC_{50}$s against HIV-1 subtypes (A-G, O) ranged from 1600 to 4900 nM (VIREAD® package insert 2007). $IC_{50}$s against NRTI resistant HIV in a PHENOSENSE™ assay ranged from <1-57 nM (median of 359-fold more potent than tenofovir (range 295-472)). $IC_{50}$s against NRTI resistant HIV in peripheral blood mononuclear cells (PBMCs) ranged from 2-19 nM (500-1000-fold more potent than tenofovir).

Test materials were provided as dry powders and were solubilized at 10 mM in water. Test materials were evaluated at a 10 µM high test concentration and serially diluted half-logarithmic increments in the in vitro antiviral assay. AZT was obtained from the NIH AIDS Research and Reference Reagent Program and was solubilized at 1 mM in water.

2. Anti-HIV-1 Cytoprotection Assay (1) Cell Preparation

CEM-SS cells were passaged in T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $5 \times 10^4$ cells per ml in tissue culture medium and added to the drug-containing microtiter plates in a volume of 50 µL.

(2) Virus Preparation

The virus used for the assay was the lymphocyte-tropic virus strain HIV-1$_{IIIB}$. The virus was obtained from the NIH AIDS Research and Reference Reagent Program and was grown in CEM-SS cells for the production of stock virus pools. A pretitered aliquot of virus was removed from the freezer (−80° C.) and allowed to thaw slowly to room temperature in a biological safety cabinet. Virus was resuspended and diluted into tissue culture medium such that the amount of virus added to each well in a volume of 50 µL was the amount determined to yield 85 to 95% cell killing at 6 days post-infection.

(3) Plate Format

Each plate contained cell control wells (cells only), virus control wells (cells plus virus), drug toxicity wells (cells plus drug only), drug colorimetric control wells (drug only) as well as experimental wells (drug plus cells plus virus). Samples were tested in triplicate with five log dilutions per compound.

(4) Efficacy and Toxicity XTT

Following incubation at 37° C. in a 5% $CO_2$ incubator, the test plates were stained with the tetrazolium dye XTT (2,3-bis(2-methoxy-4-nitro-5-sulfophenyl)-5-[(phenylamino)carbonyl]-2H-tetrazolium hydroxide). XTT-tetrazolium was metabolized by the mitochondrial enzymes of metabolically active cells to a soluble formazan product, allowing rapid quantitative analysis of the inhibition of HIV induced cell killing by anti-HIV test substances. XTT solution was prepared daily as a stock of 1 mg/mL in RPMI1640. Phenazine methosulfate (PMS) solution was prepared at 0.15 mg/mL in PBS and stored in the dark at −20° C. XTT/PMS stock was prepared immediately before use by adding 40 µL of PMS per ml of XTT solution. Fifty microliters of XTT/PMS was added to each well of the plate and the plate was reincubated for 4 hours at 37° C. Plates were sealed with adhesive plate sealers and shaken gently or inverted several times to mix the soluble formazan product and the plate was read spectrophotometrically at 450/650 nm with a Molecular Devices Vmax plate reader.

(5) Data Analysis

Raw data was collected from the Softmax Pro 4.6 software and imported into a Microsoft Excel XLfit4 spreadsheet for analysis by four parameter curve fit calculations. Both antiviral activity and toxicity with a graphic representation of the data are provided in a Plate Analysis Report summarizing the individual compound activity.

3. Results

Anti-HIV-1 Evaluations:

Three metabolites (CMX157-210, CMX157-211, and CMX157-220) were evaluated in parallel with CMX157 K+ salt against the IIIB strain of HIV-1 in CEM-SS cells. The results of these assays are summarized in Table 3.

The structures of CMX157-210, CMX157-211 and CMX157-220 are shown below:

(CMX157-210)
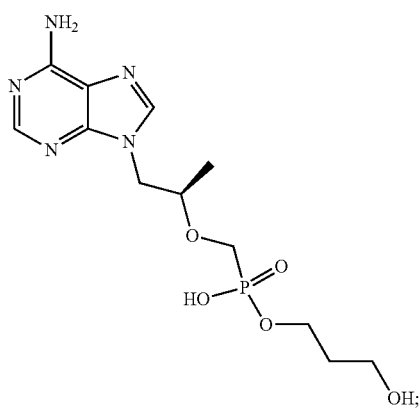

(CMX157-211)
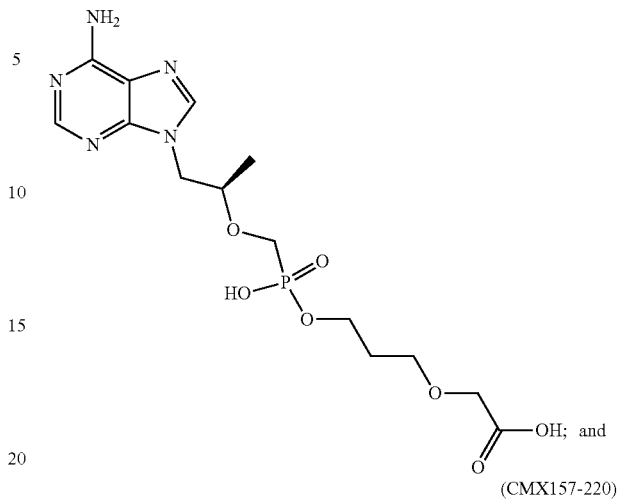

(CMX157-220)
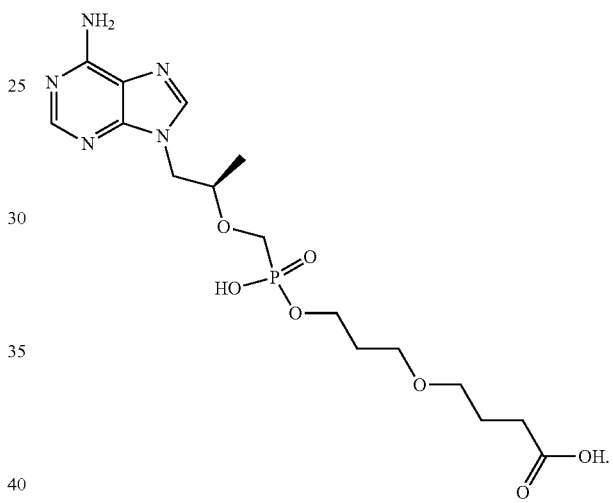

FIG. 1 depicts higher active drug levels in human PBMCs exposed to CMX157 versus tenofovir in vitro. CMX157 increases the intracellular level of tenofovir-diphosphate (TFV-PP). Points of clinical reference: 1 µM tenofovir≈human $C_{max}$ (VIREAD® package insert 2007); 0.076 pmol/$10^6$=median human TFV-PP (Kiser et al. JAIDS 2008:47) (see dashed line in FIG. 1).

Figure 2:
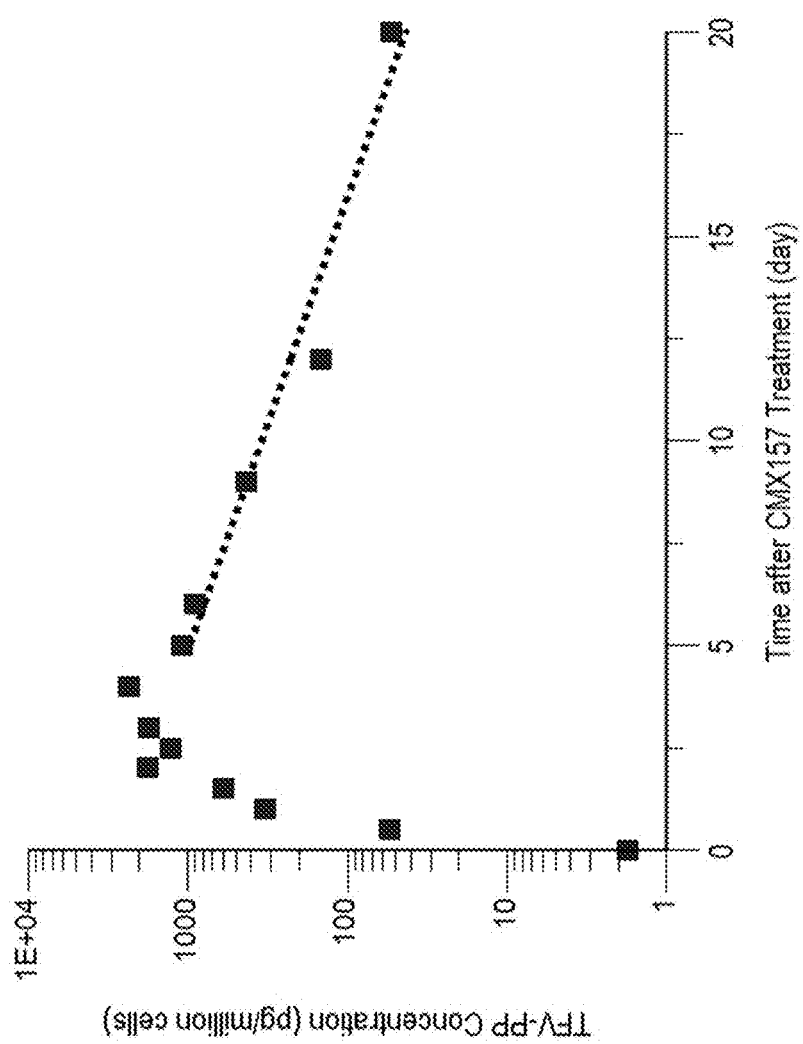
FIG. 2 depicts the in vitro intracellular half-life of tenofovir-diphosphate (TFV-PP) in human PBMCs.

FIG. 2 depicts the in vitro intracellular half-life of tenofovir-diphosphate (TFV-PP) in human PBMCs. Specifically, the concentration of TFV-PP in human PBMCs (IL-2/PHA) after in vitro incubation with 1 µM CMX157 for 48 hours, is shown ($t_{1/2}$=3.3 days).

Figure 3:
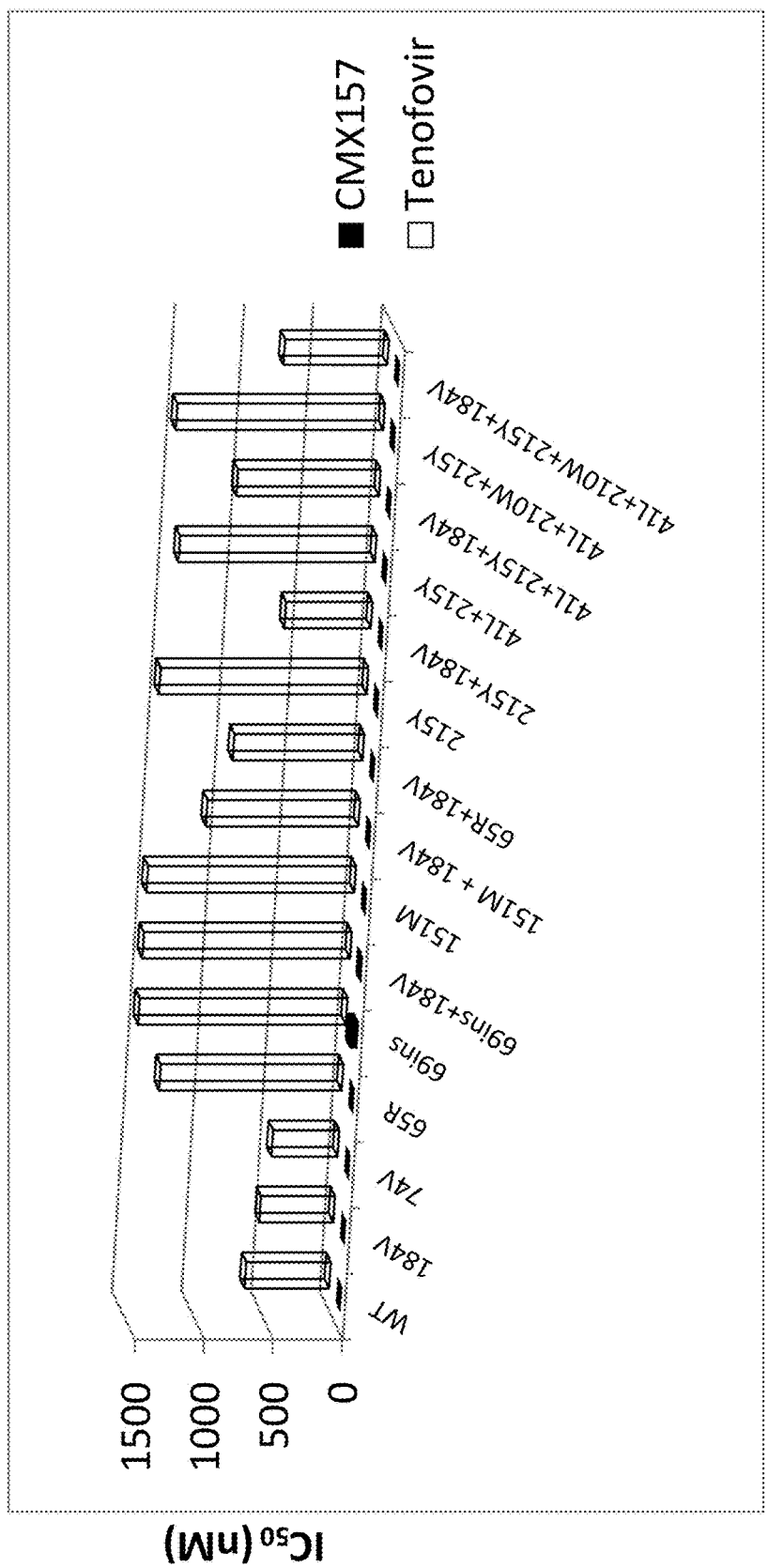
FIG. 3 shows that CMX157 is highly active against NRTI-resistant HIV isolates (PHENOSENSE™ assay).

Table 2 shows that CMX157 is highly active against NRTI-resistant HIV in PBMCs. FIG. 3 shows that CMX157 is highly active against NRTI-resistant HIV isolates (PHENOSENSE™ assay).

TABLE 2

CMX157 Activity Against NRTI-resistant HIV in PBMCs

| HIV RT Genotype | CMX157 $IC_{50}$ (nM) | Tenofovir $IC_{50}$ (nM) |
|---|---|---|
| 41L/67N/70R/215F/219E | 3.8 | 6,515 |
| 41L/67N/210W/215Y/184V | 3.1 | 5,390 |

TABLE 2-continued

CMX157 Activity Against NRTI-resistant HIV in PBMCs

| HIV RT Genotype | CMX157 $IC_{50}$ (nM) | Tenofovir $IC_{50}$ (nM) |
| --- | --- | --- |
| 41L/67N/210W/215Y | 19 | >8,509 |
| 75I/77L/116Y/151M/184V | 5.0 | >6,494 |
| 41L/210W/215Y/184V/69SSS | 9.0 | >6,469 |
| 65R/184V | 1.8 | 1,036 |

The anti-HIV assays performed met validation and standardization criteria. The AZT control compound was evaluated in parallel with the submitted test materials and yielded an $EC_{50}$ value of 3 nM, which falls within the acceptable range of activity of the control compound (1 to 10 nM). CMX157 $K^+$ salt yielded an $EC_{50}$ value of less than 30 nM with a calculated therapeutic index of greater than 173. CMX157-210, CMX157-211, and CMX157-220 did not demonstrate antiviral activity in CEM-SS cells against HIV-$1_{IIIB}$ up to a high test concentration of 10 µM.

TABLE 3

Anti-HIV Cytoprotection Assay

| Compound | CEMSS/IIIB $EC_{50}$ (µM) | CEMSS $TC_{50}$ (µM) | Therapeutic Index |
| --- | --- | --- | --- |
| AZT | 0.003 | >0.1 | >33.3 |
| CMX157 $K^+$ salt | <0.03 | 5.2 | >173.0 |
| CMX157-210 | >10.0 | >10.0 | — |
| CMX157-211 | >10.0 | >10.0 | — |
| CMX157-220 | >10.0 | >10.0 | — |

Figure 4:
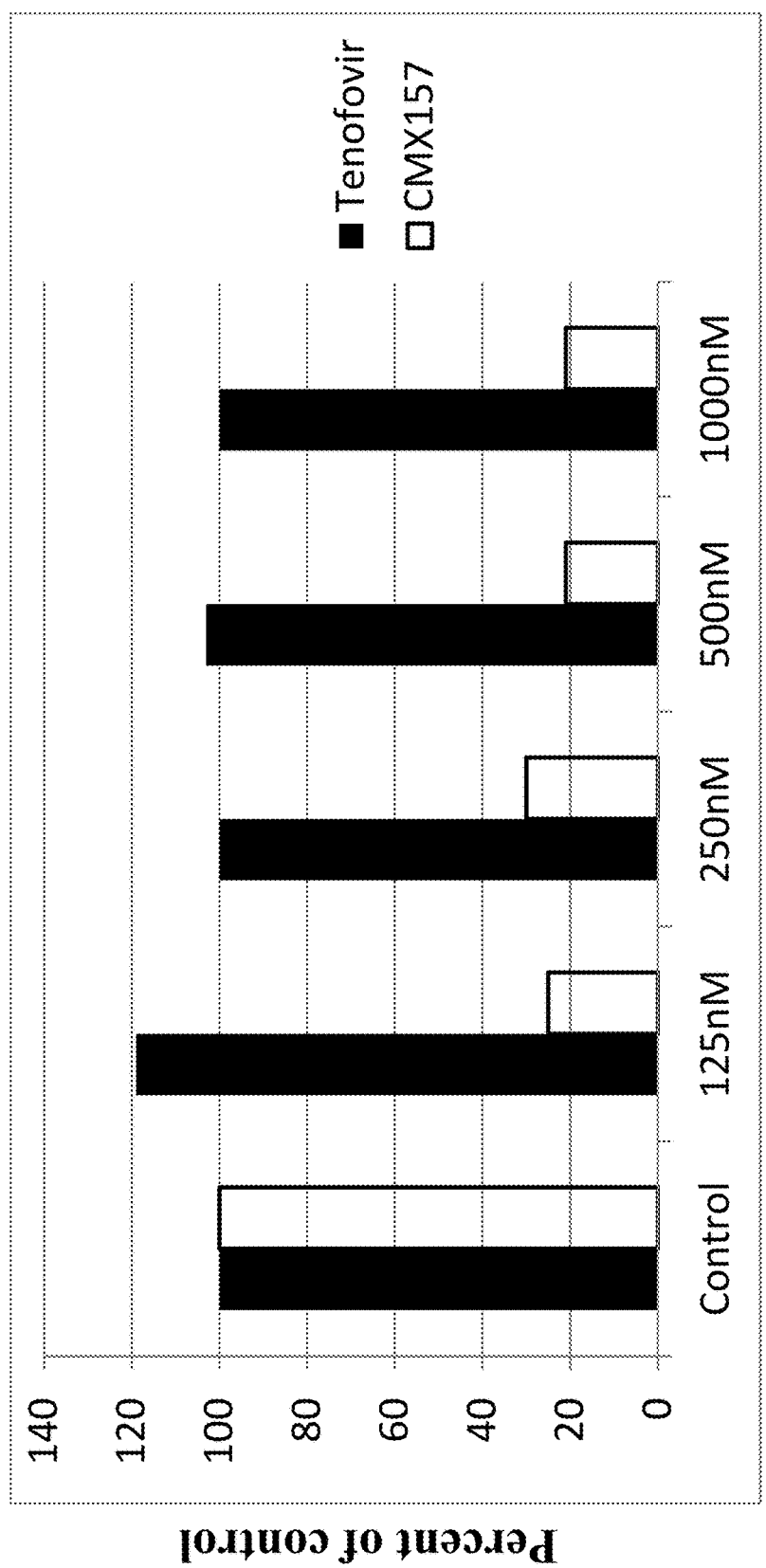
FIG. 4 depicts $TCID_{50}$ determination for HIV treated for 2 hours with tenofovir or CMX157 (p24 endpoint).
Figure 5:
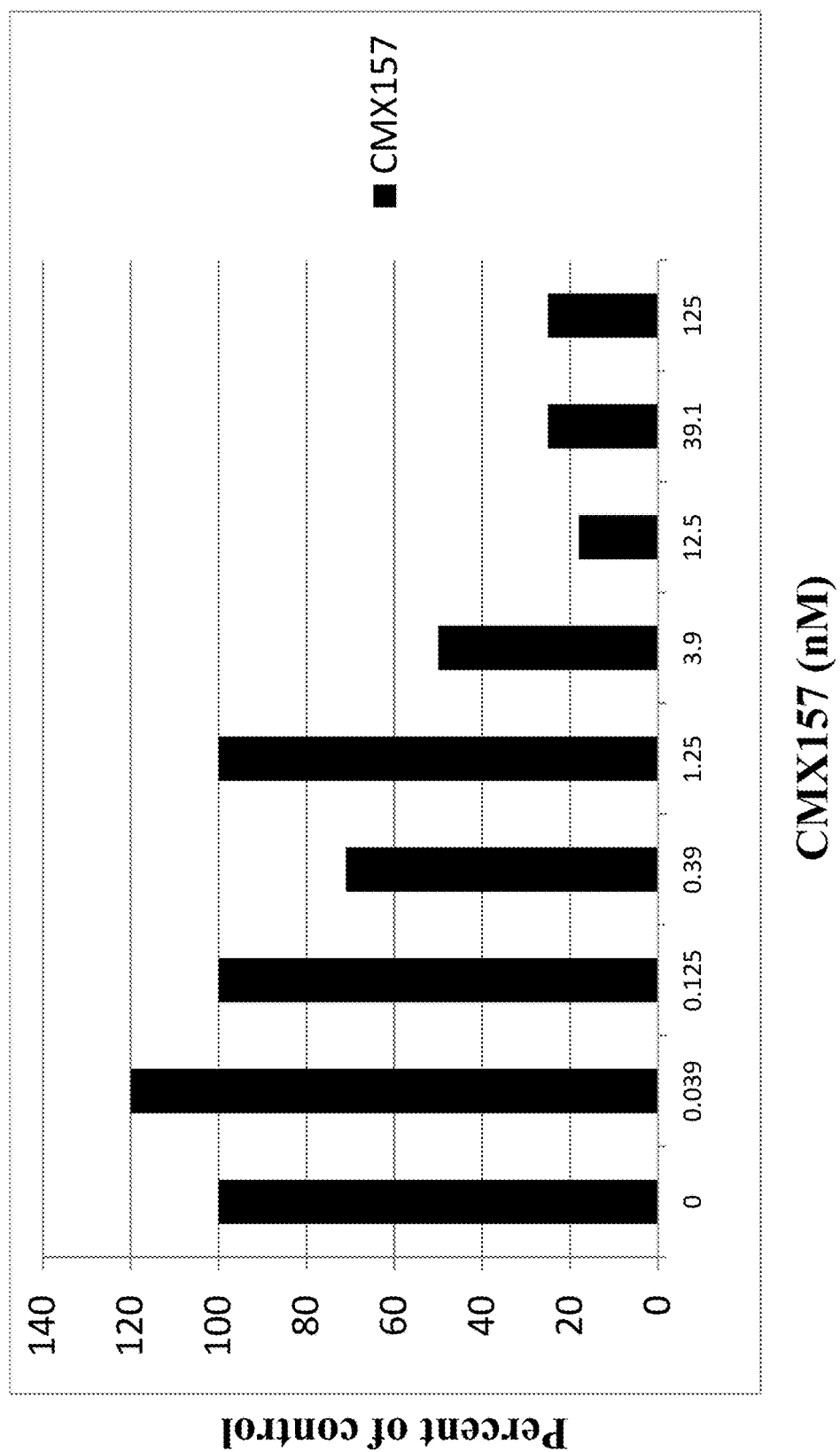
FIG. 5 depicts $TCID_{50}$ determination for HIV treated for 15 minutes with CMX157 (p24 endpoint).

FIG. 4 depicts $TCID_{50}$ determination for HIV treated for 2 hours with tenofovir or CMX157 (p24 endpoint). FIG. 5 depicts $TCID_{50}$ determination for HIV treated for 15 minutes with CMX157 (p24 endpoint).

Possible reasons for increased efficacy of CMX157 versus tenofovir are related to more active anabolite (TFV-PP) inside cells, such as direct penetration of CMX157 into cells or HIV mediated transport of CMX157 into cells. HIV replication inhibited in vitro by CMX157 delivered by HIV, which may be important for privileged compartments (e.g., CNS, semen) and microbicide use.

Table 4 depicts CMX157 and tenofovir levels in $HIV_{IIIB}$ lysates.

TABLE 4

CMX157 and Tenofovir Levels in $HIV_{IIIB}$ Lysates

| Sample | CMX157 (pmol) | Tenofovir (pmol) |
| --- | --- | --- |
| HIV + 500 nM CMX157 | 5406 | 0.3 |
| HIV + 500 nM Tenofovir | ND | 17 |
| HIV + DMSO | ND | ND |

ND = not determined

Example 2

CMX157 as a Clinical Stage Antiretroviral with Activity Against HIV and XMRV

CMX157 has been studied for safety and evaluation of pharmacokinetics in healthy volunteers in a dose-escalating single dose Phase I trial. The levels and persistence of intracellular active antiviral in the peripheral blood lymphocytes from patients in this study suggest once weekly dosing is feasible.

CMX157 is greater than 300-fold more potent than tenofovir (TFV) against HIV. For example, the CMX157 $EC_{50}$ for M41L/L210W/T215Y mutants averaged 6.3 nM versus 2,240 nM for TFV. The increase in potency may be attributed to higher concentrations of the intracellular active anabolite (TFV-diphosphate) as exemplified by the greater than 30-fold higher concentrations observed in human PBMC's incubated with 1 µM CMX157 versus 1 µM TFV (human $C_{max}$ for TFV). These data are extended to murine retroviruses associated with Chronic Fatigue Syndrome (CFS).

In Vitro Activity Against HIV

The in vitro antiviral activity profile for CMX157 was evaluated for cell-type effects and HIV strain effects. It is active against all major subtypes of HIV-1 in PBMCs with $EC_{50}$ values ranging between 0.20 and 7.18 nanomolar (nM). In a PHENOSENSE™ assay, $EC_{50}$s for CMX157 ranged from 0.66 nM for 74V/184V to 57 nM for 62V/69SVG/75I/215I; corresponding $EC_{50}$s for tenofovir were 227 nM and 16,959 nM respectively (see FIG. 3). CMX157 $IC_{50}$s for 41L/210W/215Y averaged 6.3 nM without 184V and 2.2 nM with 184V (2,240 and 770 nM for tenofovir respectively).

XMRV Cytoprotection Assay

An XMRV antiviral cytoprotection assay was conducted using PG-4 cells (ATCC# CRL-2032; feline astrocytes) and XMRV was collected from the supernatant of 22Rv1 human prostate cancer cells (ATCC# CRL-2505). Inhibition of cytopathic effect was quantified using XTT following a 6 day assay. Ribavirin and AZT were evaluated in parallel as control compounds. CMX157 $EC_{50}$s for XMRV ranged from 3 nM to 500 nM while for TFV the range was 2,400 nM to 39,100 nM.

CMX157 Study

The study was a randomized, blinded, dose escalation trial to evaluate safety, tolerability, and pharmacokinetics. Healthy volunteers in each cohort (6 active/2 placebo) received a single dose of 25, 50, 100, 200 or 400 mg. An additional cohort received a standard dose of Viread for comparison of TFV-PP levels. For tenofovir anabolite analysis, PBMCs were lysed with 70% ice cold methanol and centrifuged; supernatants were analyzed using LC/MS/MS. The clinical samples were split into two aliquots. One aliquot was used for analysis of CMX157; following addition of an internal standard, these samples were evaporated to dryness prior to reconstitution and analysis. The second aliquot was for analysis of TFV, TFV-monophosphate and TFV-diphosphate; following addition of internal standards, samples were vortexed and centrifuged prior to analysis.

Results

CMX157 was well tolerated in subjects given single doses of CMX157 ranging from 25 mg to 400 mg. There were no trends noted in clinical laboratory results, vital signs, or ECG parameters during the course of this study. No SAEs or remarkable AEs were reported. Events were mostly mild constitutional symptoms, and there was no dose relationship. Only mild headache was reported by more than one subject (n=3) taking CMX157.

Figure 6:
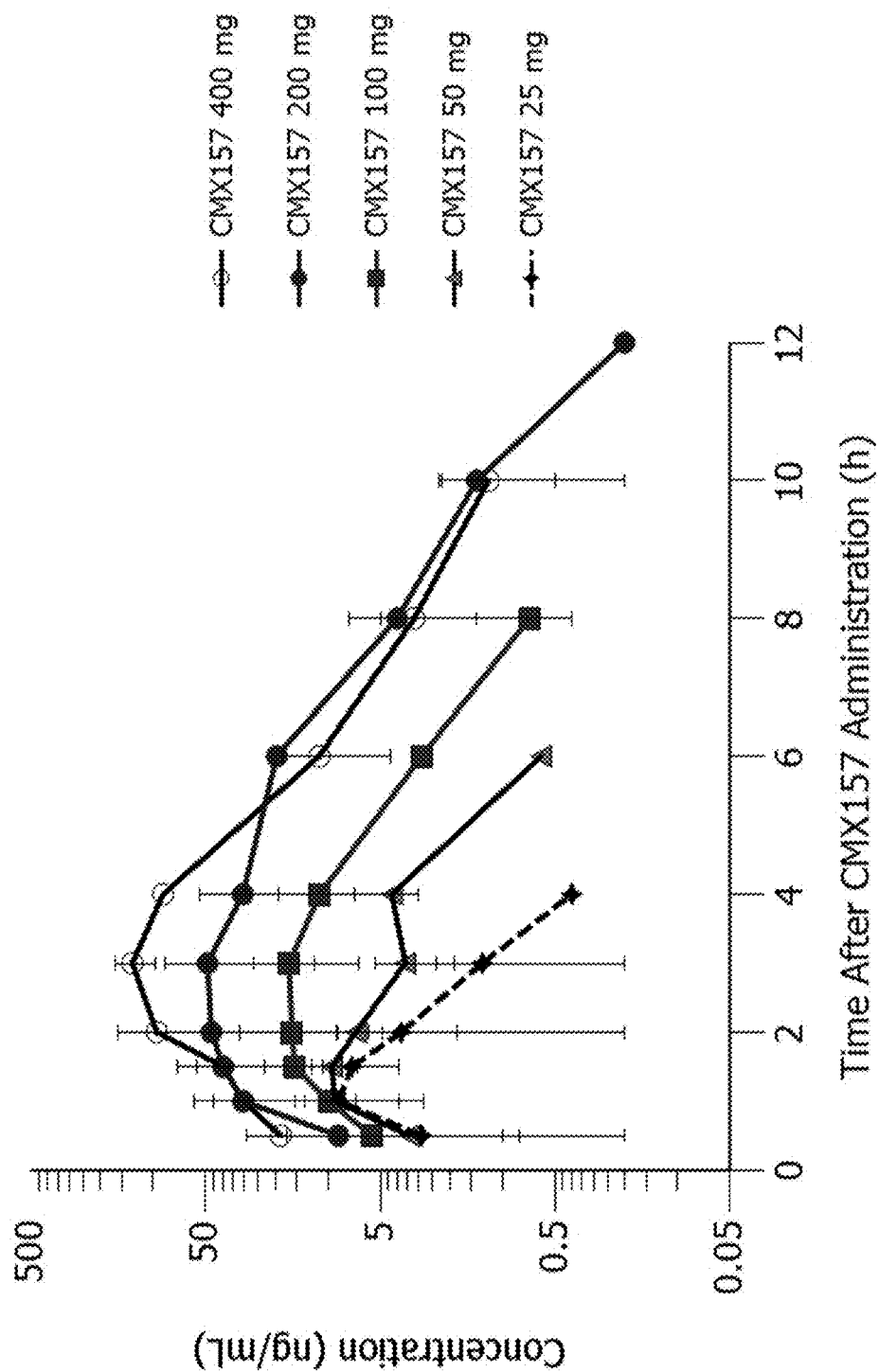
FIG. 6 depicts the plasma concentrations of CMX157 after single dose oral administration of CMX157.
Figure 7:
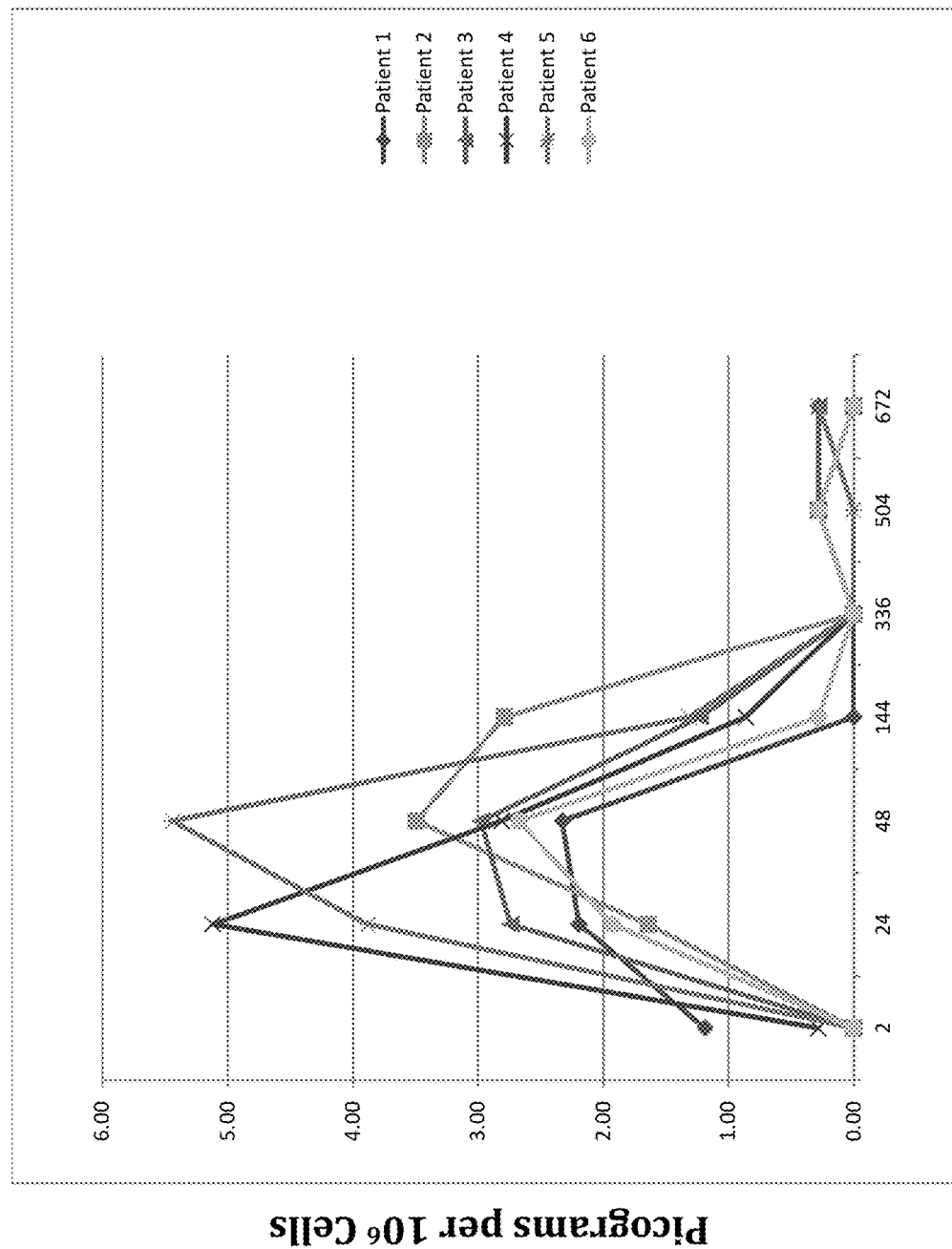
FIG. 7 depicts active antiviral (TFV-diphosphate) produced by a single 400 mg dose of CMX157 in PBMCs of healthy volunteers.

There was an approximate linear increase in CMX157 plasma $C_{max}$ and AUC with increasing dose from 25 mg to 400 mg. The data are shown below, in Table 5, for the two highest doses. FIG. 6 depicts the plasma concentrations of CMX157 after single dose oral administration of CMX157. FIG. 7 depicts active antiviral (TFV-diphosphate) produced by a single 400 mg dose of CMX157 in PBMCs of healthy volunteers. TFV-diphosphate was measurable in all subjects in the 400 mg single dose CMX157 group and all but one had detectable levels 6 days after dosing.

TABLE 5

$C_{max}$ and $AUC_{INF}$ values for CMX157 and Tenofovir

| CMX157 dose | | $C_{max}$ (ng/mL) CMX157 | $AUC_{INF}$ (h*ng/mL) | $C_{max}$ (ng/mL) TFV | $AUC_{INF}$ (h*ng/mL) |
|---|---|---|---|---|---|
| 200 mg | N | 6 | 6 | 6 | 4 |
| | Mean | 74 | 210 | 16 | 283 |
| | SD | 28 | 85 | 2.4 | 47 |
| 400 mg | N | 6 | 6 | 6 | 6 |
| | Mean | 165 | 376 | 27 | 371 |
| | SD | 64 | 124 | 4 | 59 |

Target clinical plasma levels were previously estimated by comparison of the amount of active antiviral (TFV-diphosphate) produced in PBMCs incubated with TFV or CMX157 in vitro. Treatment of activated human PBMCs with a level of TFV that approximates the human $C_{max}$ of TFV (1 μM) produced 50 fmoles of TFV-diphosphate per million cells. Similar levels of TFV-diphosphate (70 fmoles per million cells) were reached with 10 nM CMX157 (Lanier 2010). The median level of TFV-diphosphate in patients taking VIREAD® is 76 fmoles/million PBMCs (Kiser 2008). Notably, this TFV-diphosphate steady state appears to require considerable time on VIREAD®, perhaps more than 4 months (Jansen 2010). $C_{max}$ levels above 10 nM were achieved with all single dose groups, suggesting the doses evaluated may be in the right range for studies in HIV infected patients.

These data combined with prior data showing nanomolar in vitro potency, direct binding to HIV and penetration into privileged compartments make CMX157 a unique candidate NRTI for therapeutic and microbicide indications in HIV. Rapid and efficient intracellular uptake leads to high intracellular levels of active antiviral which is likely to overcome TFV resistance. Additionally, CMX157 may prove highly valuable in combination therapy for CFS against the murine retroviruses that current evidence suggests are etiologic agents of this syndrome.

Summary

CMX157 is effective in vitro against all clinically important drug resistant HIV strains, including isolates that are unresponsive to tenofovir (TFV). CMX157 is highly potent in vitro against XMRV, a virus associated with chronic fatigue syndrome, and may prove to be an effective therapy for this disorder. CMX157 single-dose administration was well tolerated and there were no laboratory, vital sign, ECG changes or AE trends attributable to CMX157. Plasma concentrations of CMX157 increased linearly with dose and target levels were attained at all doses. Active antiviral (TFV-diphosphate) was measurable in PBMCs from all patients after a single 400 mg dose of CMX157 (but not after a single standard dose of VIREAD®) and remained detectable for 6 days, suggesting the possibility for infrequent (for example, weekly) dosing. CMX157 could enable multiple once-a-day (i.e., QD) or weekly (i.e., QW) one pill dosing regimens for HIV treatment.

Example 3

CMX157 and Human Organic Anion Transporters

A study was completed to assess whether or not CMX157 and tenofovir (CMX167) were substrates for human OAT1 (organic anion transporter') or OAT3 (organic anion transporter3). For comparison, probenecid, an established inhibitor of organic anion transporters, was included in the study as a reference inhibitor.

Figure 8:
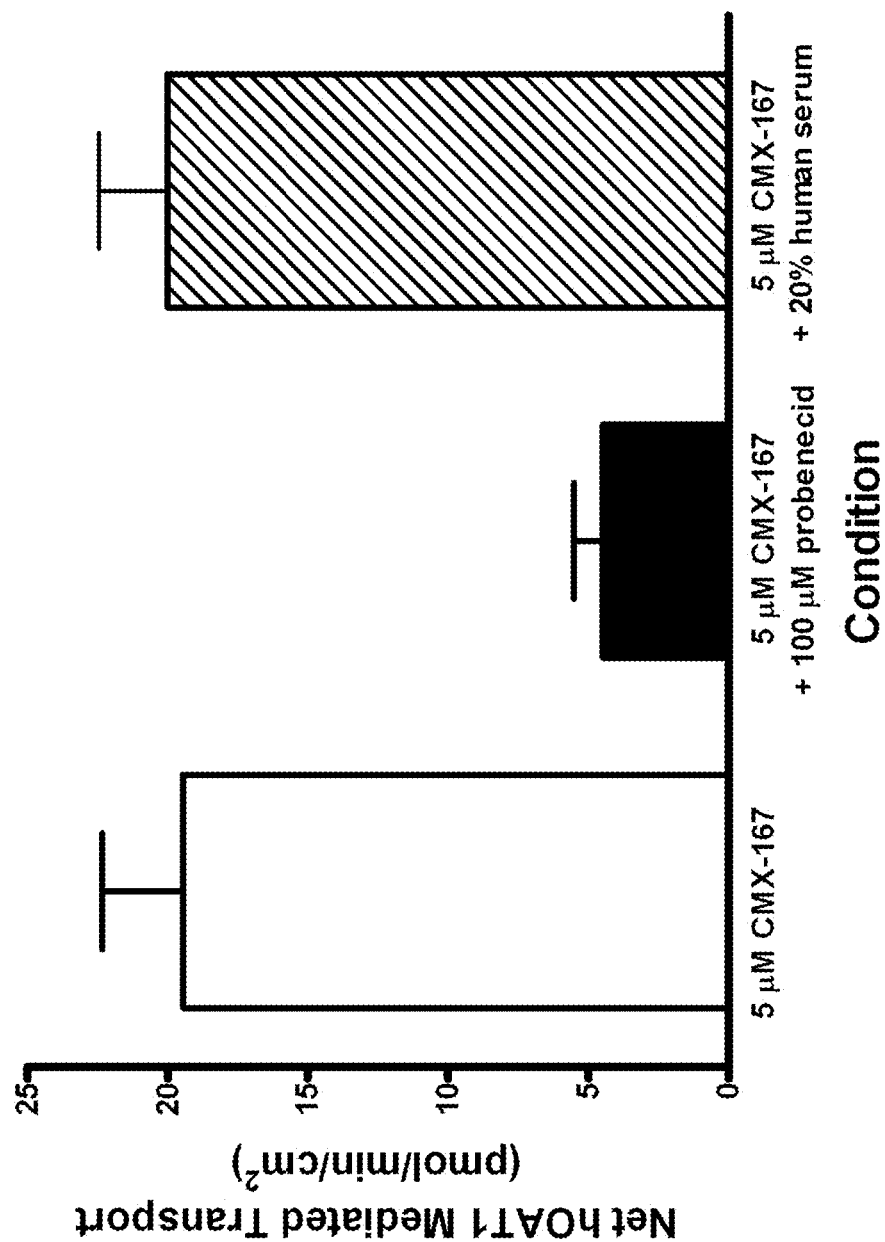
FIG. 8 depicts net hOAT1 mediated tenofovir (CMX167) transport in the absence or presence of 100 μM probenecid and 20% human serum.

Tenofovir appeared to be a substrate for human OAT1. Tenofovir showed significant hOAT1 mediated transport that was inhibited by 100 μM probenecid. The presence of 20% human serum did not significantly alter the OAT1 mediated transport of tenofovir. FIG. 8 depicts net hOAT1 mediated tenofovir transport in the absence or presence of 100 μM probenecid and 20% human serum.

Figure 9:
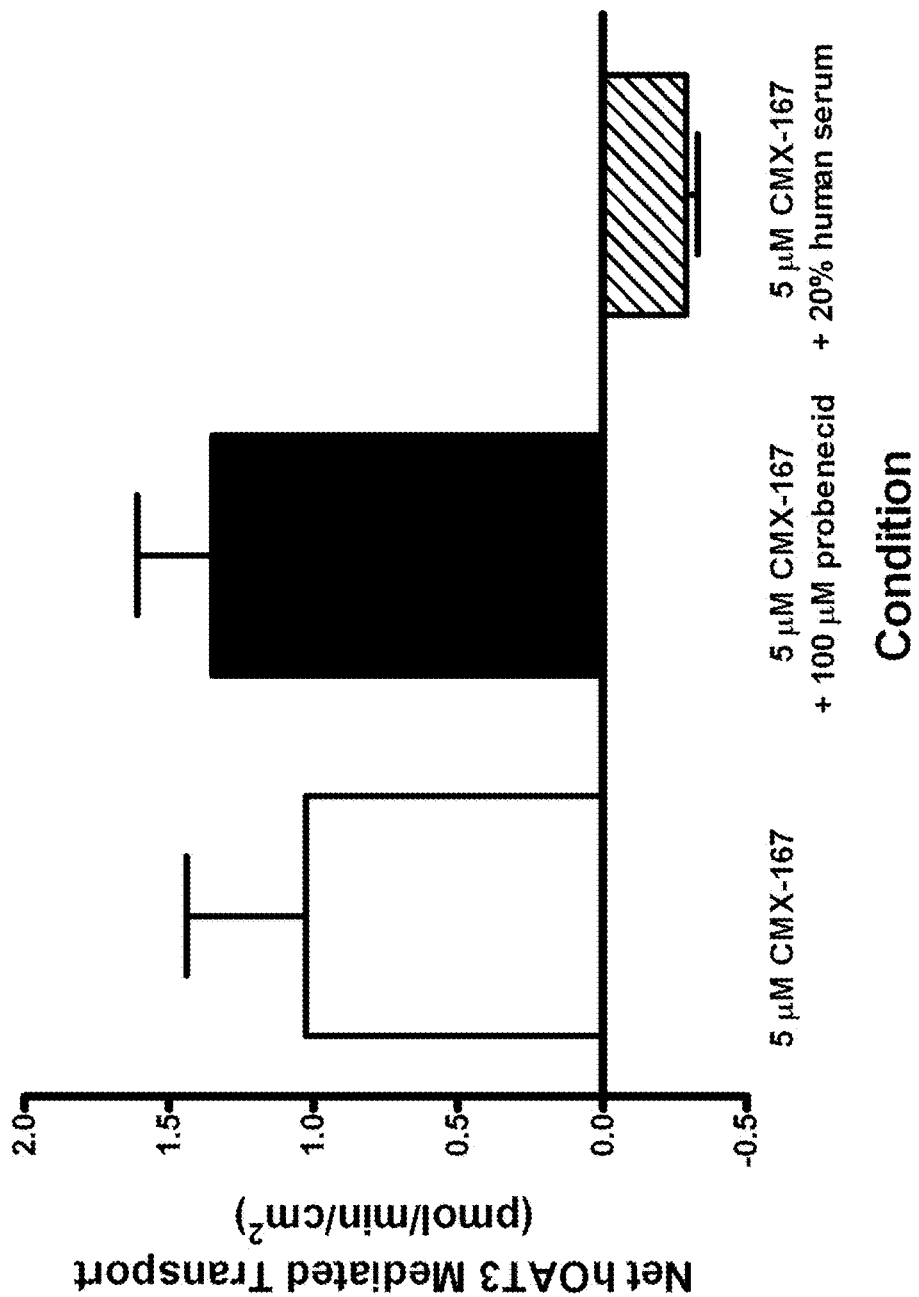
FIG. 9 depicts net hOAT3 mediated tenofovir (CMX167) transport in the absence or presence of 100 μM probenecid and 20% human serum.

Tenofovir appeared to be a modest substrate for human OAT3. The OAT3 mediated transport was not noticeably altered in the presence of 100 μM probenecid however. The presence of 20% human serum appeared to reduce the modest net transport of tenofovir. FIG. 9 depicts net hOAT3 mediated tenofovir transport in the absence or presence of 100 μM probenecid and 20% human serum. Table 6 shows data for assessing transport of tenofovir by hOAT1 and hOAT3.

TABLE 6

In vitro assay data for study assessing transport of tenofovir by hOAT1 and hOAT3.

| Name | Cellular Accumulation (transporter) (pmol/min/cm$^2$) | Cellular Accumulation (control) (pmol/min/cm$^2$) | Net Transporter Mediated Cellular Accumulation (pmol/min/cm$^2$) |
|---|---|---|---|
| hOAT1 | | | |
| Tenofovir | 21.9 ± 4.04 | 2.45 ± 0.197 | 19.5 ± 4.04 |
| Tenofovir + probenecid | 6.71 ± 1.46 | 2.22 ± 0.995 | 4.49 ± 1.46 |
| Tenofovir + serum | 21.8 ± 3.45 | 1.77 ± 1.13 | 20.0 ± 3.45 |
| hOAT3 | | | |
| Tenofovir | 3.68 ± 0.591 | 2.65 ± 1.96 | 1.03 ± 0.591 |
| Tenofovir + probenecid | 3.29 ± 0.364 | 1.94 ± 0.345 | 1.35 ± 0.364 |
| Tenofovir + serum | 1.99 ± 0.0591 | 2.28 ± 1.24 | −0.292 ± 0.0591 |

Figure 10:
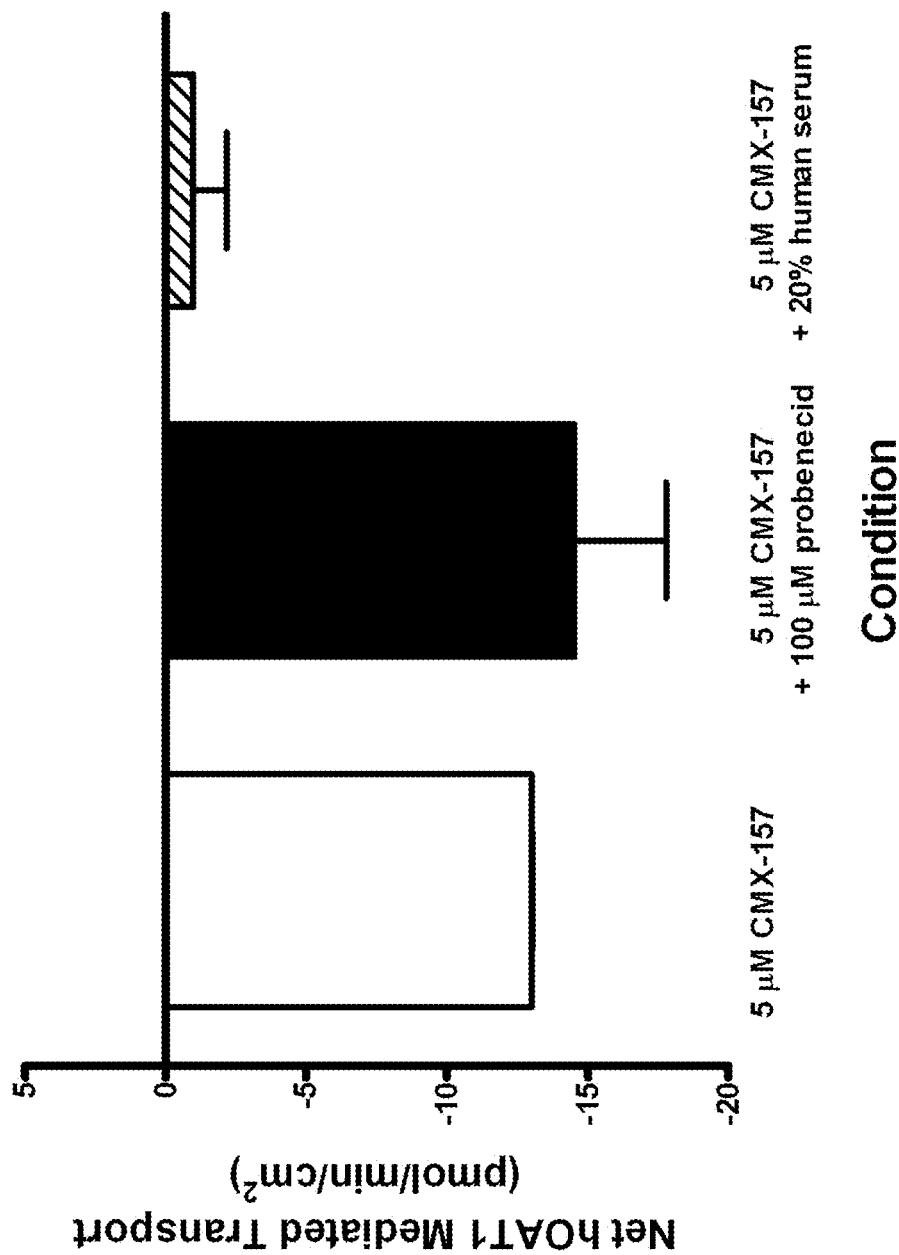
FIG. 10 depicts net hOAT1 mediated CMX157 transport in the absence or presence of 100 μM probenecid and 20% human serum.

CMX157 did not appear to be a substrate for human OAT1. The presence of 100 μM probenecid did not provide any further insight. The presence of 20% human serum significantly reduced the cellular accumulation of CMX157 in both the OAT1 expressing cells as well as the control cells. FIG. 10 depicts net hOAT1 mediated CMX157 transport in the absence or presence of 100 μM probenecid and 20% human serum.

Figure 11:
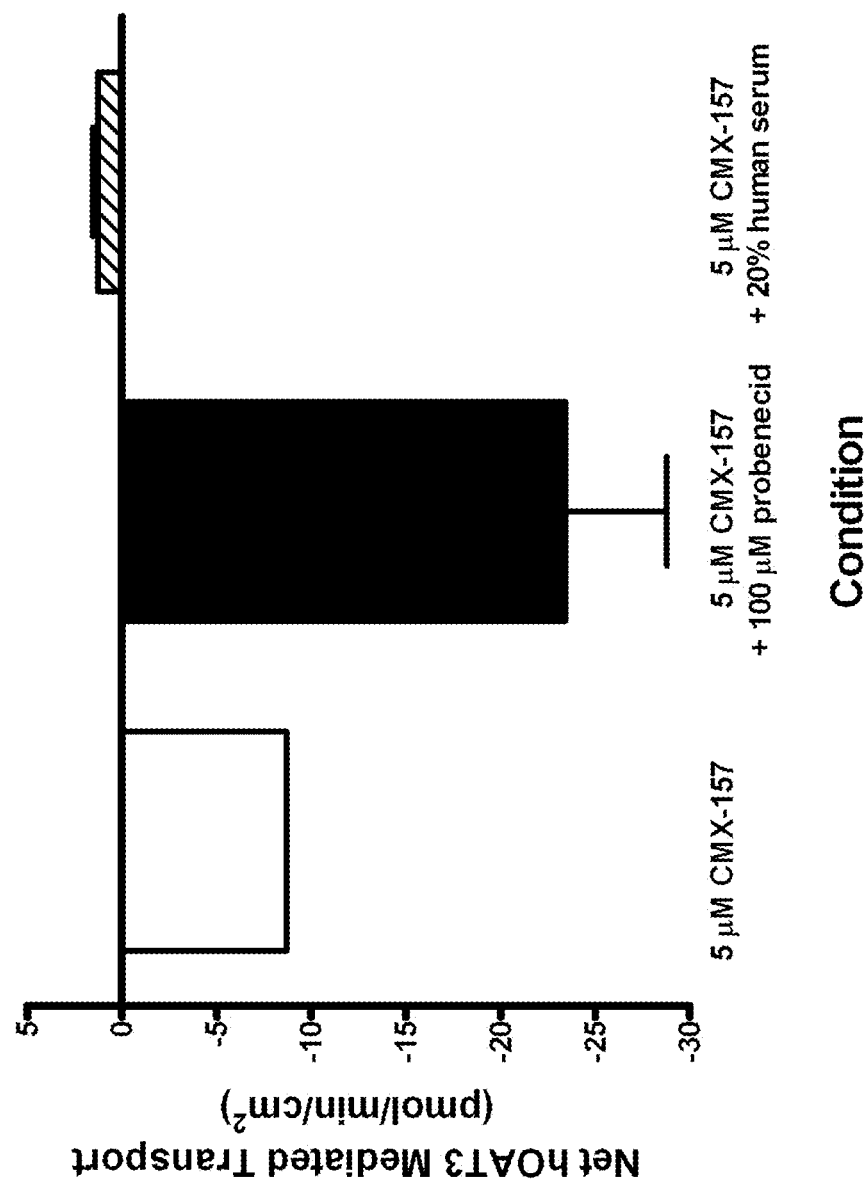
FIG. 11 depicts net hOAT3 mediated CMX157 transport in the absence or presence of 100 μM probenecid and 20% human serum.

CMX157 did not appear to be a substrate for human OAT3. The presence of 100 μM probenecid did not provide any further insight. The presence of 20% human serum significantly reduced the cellular accumulation of CMX157 in both the OAT3 expressing cells as well as the control cells. FIG. 11 depicts net hOAT3 mediated CMX157 transport in the absence or presence of 100 μM probenecid and 20% human serum (one value excluded from 5 μM CMX157 condition). Table 7 shows data for assessing transport of CMX157 by hOAT1 and hOAT3.

TABLE 7

In vitro assay data for study assessing
transport of CMX157 by hOAT1 and hOAT3.

| Name | Cellular Accumulation (transporter) (pmol/min/cm$^2$) | Cellular Accumulation (control) (pmol/min/cm$^2$) | Net Transporter Mediated Cellular Accumulation (pmol/min/cm$^2$) |
|---|---|---|---|
| hOAT1 | | | |
| CMX157 | 37.3 ± 0.0465 | 50.3 ± 1.30 | −13.0 ± 0.0465 |
| CMX157 + probenecid | 25.9 ± 4.65 | 40.4 ± 5.17 | −14.5 ± 4.65 |
| CMX157 + serum | 5.51 ± 1.70 | 6.46 ± 0.168 | −0.954 ± 1.70 |
| hOAT3 | | | |
| CMX157 | 30.7 | 39.5 ± 11.6 | −8.72 |
| CMX157 + probenecid | 26.1 ± 7.59 | 49.5 ± 2.65 | −23.4 ± 7.59 |
| CMX157 + serum | 6.16 ± 0.396 | 4.90 ± 1.57 | 1.26 ± 0.396 |

Experimental: The uptake test system was comprised of a polarized monolayer of MCDK-II cells grown on permeable supports. The MDCK-II cells were treated to express the transporter of interest or treated with a control vector.

The uptake of 2 μM [$^3$H]-p-aminohippurate (PAH) and 0.75 μM [$^3$H]-estrone-3-sulfate (E-3-S) in the absence and presence of the reference inhibitor was determined by radiometric detection. The uptake of CMX157 and tenofovir was in the absence and presence of the reference inhibitor or 20% human serum was determined by LC/MS/MS. Experiments were performed under the same conditions for the cells expressing the transporter or those treated with the control vector.

Net transporter mediated uptake of substrate is calculated by subtracting uptake in the control system, which does not express the transporter of interest, from uptake in the test system which does express the transporter of interest.

Net Transporter Mediated Uptake=(Cellular accumulation in the presence of the transporter)−(Cellular accumulation in the absence of the transporter)

Results: The net hOAT1 mediated uptake of tenofovir in the presence and absence of 100 μM probenecid or 20% human serum is shown in FIG. 8. The transport of tenofovir is inhibited by probenecid and relatively unchanged by the presence of 20% human serum. OAT3 also appeared to mediate the transport of tenofovir. The effect of probenecid, however, was minimal. The presence of 20% human serum in the OAT3 experiment reduced the OAT3 mediated transport of tenofovir.

The net hOAT1 mediated uptake of CMX157 in the presence and absence of 100 μM probenecid or 20% human serum is shown in FIG. 10. There is no apparent transport of CMX157. The presence of 20% human serum significantly reduces the cellular accumulation of CMX157 in both control and transporter expressing cells. Tenofovir did not appear to be a substrate of hOAT3 either. The presence of 20% human serum significantly reduces the cellular accumulation of CMX157 in both control and transporter expressing cells.

Figure 12:
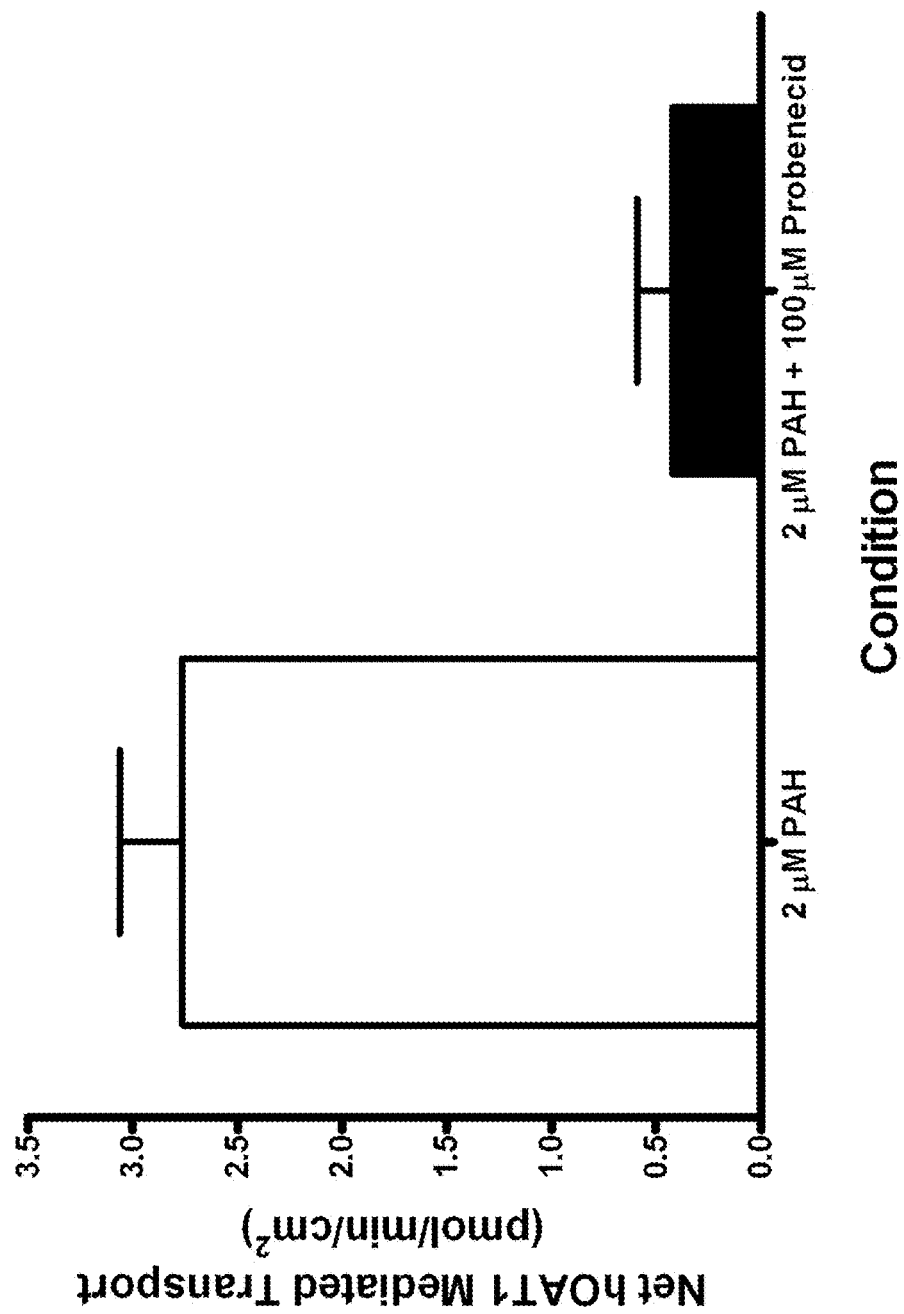
FIG. 12 illustrates the hOAT1 mediated transport of PAH and inhibition thereof by probenecid, indicating a working hOAT1 system.
Figure 13:
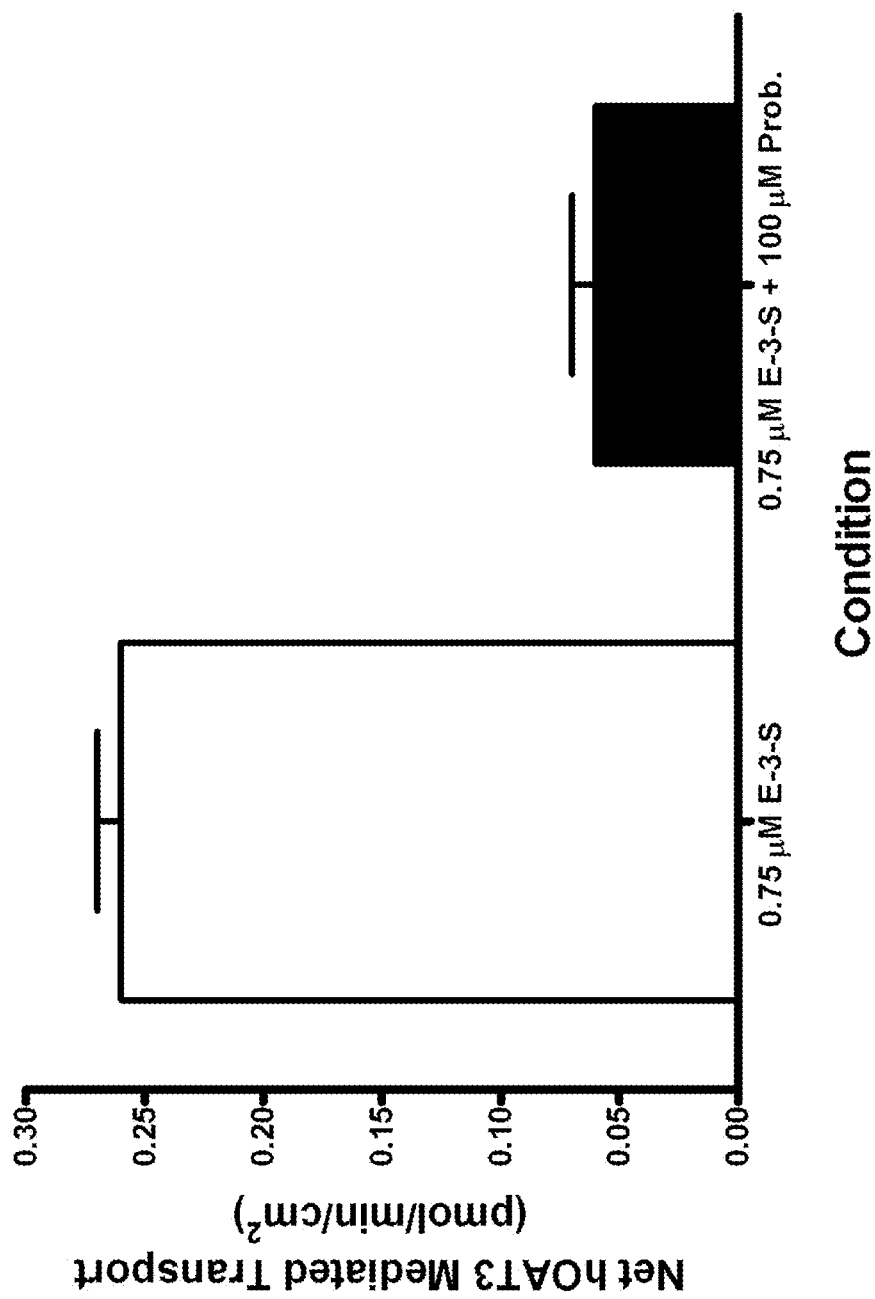
FIG. 13 illustrates the hOAT3 mediated transport of E-3-S and inhibition thereof by probenecid, indicating a working hOAT3 system.

The result for the control assays for human OAT1 and OAT3 are shown in FIGS. 12 and 13 and Table 8. FIG. 12 illustrates the hOAT1 mediated transport of PAH and inhibition thereof by probenecid, indicating a working hOAT1 system. FIG. 13 illustrates the hOAT3 mediated transport of E-3-S and inhibition thereof by probenecid, indicating a working hOAT3 system.

TABLE 8

In vitro assay data for probe substrates and the reference inhibitor

| Name | Cellular Accumulation (transporter) (pmol/min/cm$^2$) | Cellular Accumulation (control) (pmol/min/cm$^2$) | Net Transporter Mediated Cellular Accumulation (pmol/min/cm$^2$) |
|---|---|---|---|
| hOAT1 | | | |
| 2 μM PAH | 2.97 ± 0.418 | 0.210 ± 0.0281 | 2.76 ± 0.418 |
| 2 μM PAH + probenecid | 0.686 ± 0.241 | 0.264 ± 0.160 | 0.422 ± 0.241 |
| hOAT3 | | | |
| 0.75 μM E3S | 30.7 | 39.5 ± 11.6 | −8.72 |
| CMX157 + probenecid | 26.1 ± 7.59 | 49.5 ± 2.65 | −23.4 ± 7.59 |
| CMX157 + serum | 6.16 ± 0.396 | 4.90 ± 1.57 | 1.26 ± 0.396 |

Conclusions: Tenofovir appeared to be a substrate for human OAT1 and, to a lesser extent, OAT3. Tenofovir transport was inhibited by 100 μM probenecid. The effects of 20% human serum on tenofovir transport were not large.

CMX157 did not appear to be a substrate for human OAT1 or OAT3. The presence of 100 μM probenecid did not provide any further insight into the mechanism of cellular accumulation of CMX157. The presence of 20% human serum significantly reduced the cellular accumulation of CMX157 in the OAT1 expressing cells, the OAT3 expressing cells, and the control cells.

The effect was largely absent in the presence of 20% human serum. The presence of serum may significantly reduce non-specific interaction of CMX157 with the plasma membrane, or proteins therein, by shifting the non-specific interactions to the serum proteins. It is possible that the expression of the transporters changes the membrane in a way that reduces the non-specific cellular accumulation of CMX157 in the transporter expressing cells relative to the control cells and this accumulation is largely abrogated by the presence of 20% human serum. This could be due to differences in the expression of other membrane proteins (that bind CMX157) in the transporter expressing cells versus that of the control cells.

These data support the conclusion that CMX157 has a low potential to cause OAT-mediated nephrotoxicity, a known adverse event following administration of tenofovir.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed and that modifications to the disclosed embodiments, as well as other embodiments, are intended to be included within the scope of the appended claims. The invention is defined by the following claims, with equivalents of the claims to be included therein.

What is claimed is:

1. A method of treating a retroviral infection in a subject, comprising administering to the subject in need thereof a therapeutically effective amount of a compound of the structure:

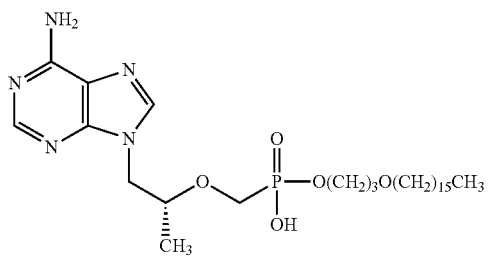

or a pharmaceutically acceptable salt thereof;
wherein the compound or the pharmaceutically acceptable salt thereof is administered to the subject daily or weekly in an amount of about 25 mg to about 2000 mg.

2. The method of claim 1, wherein the retroviral infection is an HIV infection.

3. The method of claim 1, wherein the retroviral infection is an HBV infection.

4. The method of claim 2, wherein the subject is also infected with HBV.

5. The method of claim 3, wherein the subject is also infected with HIV.

6. The method of claim 1, wherein the compound or the pharmaceutically acceptable salt thereof is administered to the subject daily.

7. The method of claim 6, wherein the daily dose is administered to the subject as a single dose once daily.

8. The method of claim 6, wherein the daily dose is divided into two to four doses per day.

9. The method of claim 6, wherein the compound or the pharmaceutically acceptable salt thereof is administered to the subject once per day for 1, 2, 3, 4, 5, 6, 7, 8, 9, or 10 days or more.

10. The method of claim 1, wherein the compound or the pharmaceutically acceptable salt thereof is administered to the subject weekly.

11. The method of claim 10, wherein the compound or the pharmaceutically acceptable salt thereof is administered to the subject once per week for 1, 2, 3, 4, 5, 6, 7, 8, 9, or 10 weeks or more.

12. The method of claim 1, wherein the compound or the pharmaceutically acceptable salt thereof is administered to the subject in an amount of about 25 mg, about 50 mg, about 75 mg, about 100 mg, or about 200 mg.

13. The method of claim 1, wherein the compound or the pharmaceutically acceptable salt thereof is administered to the subject in an amount of about 25 mg, or about 50 mg.

14. The method of claim 6, wherein the compound or the pharmaceutically acceptable salt thereof is administered to the subject in an amount of about 25 mg, about 50 mg, about 75 mg, about 100 mg, or about 200 mg.

15. The method of claim 6, wherein the compound or the pharmaceutically acceptable salt thereof is administered to the subject in an amount of about 25 mg, or about 50 mg.

16. The method of claim 10, wherein the compound or the pharmaceutically acceptable salt thereof is administered to the subject in an amount of about 25 mg, about 50 mg, about 75 mg, about 100 mg, or about 200 mg.

17. The method of claim 10, wherein the compound or the pharmaceutically acceptable salt thereof is administered to the subject in an amount of about 25 mg, or about 50 mg.

18. The method of claim 1, further comprising concurrently administering to the subject one or more additional antiviral agents with the compound or the pharmaceutically acceptable salt thereof.

19. The method of claim 18, wherein the one or more additional antiviral agents is selected from the group consisting of HIV-protease inhibitors, nucleoside reverse transcriptase inhibitors, non-nucleoside reverse transcriptase inhibitors, integrase inhibitors, entry inhibitors, fusion inhibitors, maturation inhibitors, and combinations thereof.

20. The method of claim 18, wherein the one or more additional antiviral agents is selected from the group consisting of lamivudine, abacavir, zidovudine, stavudine, zalcitabine, didanosine, emtricitabine, tenofovir, delavirdine, efavirenz, etravirine, nevirapine, amprenavir, atazanavir, darunavir, indinavir, lopinavir, nelfinavir, ritonavir, saquinavir, tipranavir, maraviroc, enfuvirtide, raltegravir, and combinations thereof.

* * * * *